US007704945B2

(12) United States Patent
Sims et al.

(10) Patent No.: US 7,704,945 B2
(45) Date of Patent: Apr. 27, 2010

(54) IL-18 RECEPTORS

(75) Inventors: John E. Sims, Seattle, WA (US); Teresa L. Born, Kenmore, WA (US)

(73) Assignee: Immunex Corporation, Thousand Oaks, CA (US)

(*) Notice: Subject to any disclaimer, the term of this patent is extended or adjusted under 35 U.S.C. 154(b) by 381 days.

(21) Appl. No.: 11/699,676

(22) Filed: Jan. 29, 2007

(65) Prior Publication Data
US 2007/0135625 A1 Jun. 14, 2007

Related U.S. Application Data

(60) Division of application No. 10/439,458, filed on May 15, 2003, now Pat. No. 7,169,581, which is a division of application No. 09/621,502, filed on Jul. 21, 2000, now Pat. No. 6,589,764, which is a continuation of application No. PCT/US99/01419, filed on Jan. 22, 1999.

(60) Provisional application No. 60/072,301, filed on Jan. 23, 1998, provisional application No. 60/078,835, filed on Mar. 20, 1998, provisional application No. 60/094,469, filed on Jul. 28, 1998.

(51) Int. Cl.
*A61K 38/00* (2006.01)
*A61K 38/20* (2006.01)
(52) U.S. Cl. .......................... 514/2; 530/350; 530/351; 435/69.7; 536/23.4
(58) Field of Classification Search ........................ None
See application file for complete search history.

(56) References Cited

U.S. PATENT DOCUMENTS

| | | | |
|---|---|---|---|
| 5,488,032 | A | 1/1996 | Dower et al. |
| 5,668,256 | A | 9/1997 | Devos et al. |
| 5,776,731 | A | 7/1998 | Parnet et al. |
| 5,844,099 | A | 12/1998 | Stahl et al. |
| 5,853,721 | A | 12/1998 | Gately et al. |
| 6,087,116 | A | 7/2000 | Torigoe et al. |
| 6,280,955 | B1 | 8/2001 | Cao |
| 6,326,472 | B1 | 12/2001 | Timans et al. |
| 6,472,179 | B2 | 10/2002 | Stahl et al. |
| 2002/0052475 | A1 | 5/2002 | Leung et al. |

FOREIGN PATENT DOCUMENTS

| | | |
|---|---|---|
| EP | 0 726 954 B1 | 8/1994 |
| EP | 0 759 466 A3 | 2/1997 |
| EP | 0 850 952 A1 | 1/1998 |
| EP | 0 864 585 A1 | 9/1998 |
| EP | 1 229 047 A2 | 8/2002 |
| WO | WO 96/13593 | 5/1996 |

OTHER PUBLICATIONS

Arend, W. P. et al., "Binding of IL-1α, IL-1β, and IL-1 receptor antagonist by soluble IL-1 receptors and levels of soluble IL-1 receptors in synovial fluids," *J. of Immunol.*, 153(10):4766-4774, 1994.

Born, T.L. et al., "Cloning of a novel receptor subunit, AcPL, required for interleukin-18 signaling," *J Biol Chem* 273(45):29445-29450, 1998.
Database EST-STS on MASPAR search, Gene Library Lab. National Institute of Genetics, (Yata 111, Mishima Shizuoka Japan), No. D76008, Kohara et al., "Toward an expression map of the *C. elegans* genome," 1995, see sequence alignment.
Dinarello, C. A., "Interleukin-1 and its biologically related cytokines," *Advances in Immunol.*, 44:153-205, 1989.
Gayle, M. A. et al., "Cloning of a putative ligand for the T1/ST2 receptor," *J. Biol. Chem.*, 271(10):5784-5789, 1996.
Greenfeder, S. A. et al., "Molecular cloning and characterization of a second subunit of the interleukin 1 receptor complex," *J. Biol. Chem.*, 270(23):13757-13765, 1995.
Liu, C. et al., "Rat homolog of mouse interleukin-1 receptor accessory protein: cloning, localization and modulation studies," *J. of Neuro.*, 66:41-48, 1996.
Micallef, M. J. et al., "Interferon-γ-inducing factor enhances T helper 1 cytokine production by stimulated human T cells: synergism with interleukin-12 for interferon-γ production," *Eur. J. Immunol.*, 26:1647-1651, 1996.
Mitcham, J. L. et al., "T1/ST2 signaling establishes it as a member of an expanding interleukin-1 receptor family," *J. of Biol. Chem.*, 271(10):5777-5783, 1996.
Novick, D. et al., "Interleukin-18 binding protein: A novel modulator of the Th1 cytokine response," *Immunity*, 10:127-136, 1999.
Okamura, H. et al., "Cloning of a new cytokine that induces IFN-γ production by T cells," *Nature*, 378:88-91, 1995.
Parnet, P. et al., "IL-1Rrp is a novel receptor-like molecule similar to the type I interleukin-1 receptor and its homologues T1/ST2 and IL-1R AcP," *J. of Biol. Chem.*, 271(8):3967-3970, 1996.
Reznikov, L. L. et al., "IL-18 binding protein increases spontaneous and IL-1-induced prostaglandin production via inhibition of IFN-γ," *PNAS*, 97(5):2174-2179, 2000.
Rothe, H. et al., "Active stage of autoimmune diabetes is associated with the expression of a novel cytokine, IGIF, which is located near *Idd2*," *J. of Clinical Investigation*, 99(3):469-474, 1997.
Sims, J. E. et al., "Genomic organization of the type I and type II IL-1 receptors," *Cytokine*, 7(6):483-490, 1995.
Thanos, D. and Maniatis, T., "NF-κB: A lesson in family values," *Cell*, 80:529-532, 1995.
Torigoe, K. et al., "Purification and characterization of the human interleukin-18 receptor," *J. of Biol. Chem.*, 272(41):25737-25742, 1997.
Tsutsui, H. et al., "IFN-γ-inducing factor up-regulates fas ligand-mediated cytotoxic activity of murine natural killer cell clones," *J. Immunol.*, 157:3967-3973, 1996.
Ushio, S. et al., "Cloning of the cDNA for human IFN-γ-inducing factor, expression in *Escherichia coli*, and studies on the biologic activities of the protein," *J. Immunol.*, 156:4274-4279, 1996.
Yoshimoto, T. et al., "Interleukin 18 together with interleukin 12 inhibits IgE production by induction of interferon-γ production from activated B cells," *Proc. Natl. Acad. Sci. USA*, 94:3948-3953, 1997.

*Primary Examiner*—Dong Jiang
(74) *Attorney, Agent, or Firm*—Thomas J. Wrona

(57) ABSTRACT

A novel polypeptide that functions as an IL-18 receptor is disclosed. The receptor is multimeric and includes at least one AcPL polypeptide, or fragment thereof, and at least one IL-1Rrp1 polypeptide, or fraction thereof. The receptor binds IL-18 and finds use in inhibiting biological activities mediated by IL-18.

13 Claims, No Drawings

SEQUENCE LISTING

```
<160> NUMBER OF SEQ ID NOS: 8

<210> SEQ ID NO 1
<211> LENGTH: 2681
<212> TYPE: DNA
<213> ORGANISM: Human AcPL
<220> FEATURE:
<221> NAME/KEY: CDS
<222> LOCATION: (484)..(2283)

<400> SEQUENCE: 1
ctctctggat aggaagaaat atagtagaac cctttgaaaa tggatatttt cacatatttt      60
cgttcagata caaaagctgg cagttactga aataaggact tgaagttcct tcctcttttt     120
ttatgtctta agagcaggaa ataaagagac agctgaaggt gtagccttga ccaactgaaa     180
```

```
gggaaatctt catcctctga aaaaacatat gtgattctca aaaaacgcat ctggaaaatt      240
gataaagaag cgattctgta gattctccca gcgctgttgg gctctcaatt ccttctgtga      300
aggacaacat atggtgatgg ggaaatcaga agctttgaga ccctctacac ctggatatga      360
atcccccttc taatacttac cagaaatgaa ggggatactc agggcagagt tctgaatctc      420
aaaacactct actctggcaa aggaatgaag ttattggagt gatgacagga acacgggaga      480 aca atg ctc tgt ttg ggc tgg ata ttt ctt tgg ctt gtt gca gga gag        528
    Met Leu Cys Leu Gly Trp Ile Phe Leu Trp Leu Val Ala Gly Glu
     1               5                  10                  15 cga att aaa gga ttt aat att tca ggt tgt tcc aca aaa aaa ctc ctt        576
Arg Ile Lys Gly Phe Asn Ile Ser Gly Cys Ser Thr Lys Lys Leu Leu
                 20                  25                  30 tgg aca tat tct aca agg agt gaa gag gaa ttt gtc tta ttt tgt gat        624
Trp Thr Tyr Ser Thr Arg Ser Glu Glu Glu Phe Val Leu Phe Cys Asp
             35                  40                  45 tta cca gag cca cag aaa tca cat ttc tgc cac aga aat cga ctc tca        672
Leu Pro Glu Pro Gln Lys Ser His Phe Cys His Arg Asn Arg Leu Ser
         50                  55                  60 cca aaa caa gtc cct gag cac ctg ccc ttc atg ggt agt aac gac cta        720
Pro Lys Gln Val Pro Glu His Leu Pro Phe Met Gly Ser Asn Asp Leu
     65                  70                  75 tct gat gtc caa tgg tac caa caa cct tcg aat gga gat cca tta gag        768
Ser Asp Val Gln Trp Tyr Gln Gln Pro Ser Asn Gly Asp Pro Leu Glu
 80                  85                  90                  95 gac att agg aaa agc tat cct cac atc att cag gac aaa tgt acc ctt        816
Asp Ile Arg Lys Ser Tyr Pro His Ile Ile Gln Asp Lys Cys Thr Leu
                100                 105                 110 cac ttt ttg acc cca ggg gtg aat aat tct ggg tca tat att tgt aga        864
His Phe Leu Thr Pro Gly Val Asn Asn Ser Gly Ser Tyr Ile Cys Arg
            115                 120                 125 ccc aag atg att aag agc ccc tat gat gta gcc tgt tgt gtc aag atg        912
Pro Lys Met Ile Lys Ser Pro Tyr Asp Val Ala Cys Cys Val Lys Met
        130                 135                 140 att tta gaa gtt aag ccc cag aca aat gca tcc tgt gag tat tcc gca        960
Ile Leu Glu Val Lys Pro Gln Thr Asn Ala Ser Cys Glu Tyr Ser Ala
145                 150                 155 tca cat aag caa gac cta ctt ctt ggg agc act ggc tct att tct tgc       1008
Ser His Lys Gln Asp Leu Leu Leu Gly Ser Thr Gly Ser Ile Ser Cys
160                 165                 170                 175 ccc agt ctc agc tgc caa agt gat gca caa agt cca gcg gta acc tgg       1056
Pro Ser Leu Ser Cys Gln Ser Asp Ala Gln Ser Pro Ala Val Thr Trp
                180                 185                 190 tac aag aat gga aaa ctc ctc tct gtg gaa agg agc aac cga atc gta       1104
Tyr Lys Asn Gly Lys Leu Leu Ser Val Glu Arg Ser Asn Arg Ile Val
            195                 200                 205 gtg gat gaa gtt tat gac tat cac cag ggc aca tat gta tgt gat tac       1152
Val Asp Glu Val Tyr Asp Tyr His Gln Gly Thr Tyr Val Cys Asp Tyr
        210                 215                 220 act cag tcg gat act gtg agt tcg tgg aca gtc aga gct gtt gtt caa       1200
Thr Gln Ser Asp Thr Val Ser Ser Trp Thr Val Arg Ala Val Val Gln
225                 230                 235 gtg aga acc att gtg gga gac act aaa ctc aaa cca gat att ctg gat       1248
Val Arg Thr Ile Val Gly Asp Thr Lys Leu Lys Pro Asp Ile Leu Asp
240                 245                 250                 255 cct gtc gag gac aca ctg gaa gta gaa ctt gga aag cct tta act att       1296
Pro Val Glu Asp Thr Leu Glu Val Glu Leu Gly Lys Pro Leu Thr Ile
                260                 265                 270 agc tgc aaa gca cga ttt ggc ttt gaa agg gtc ttt aac cct gtc ata       1344
Ser Cys Lys Ala Arg Phe Gly Phe Glu Arg Val Phe Asn Pro Val Ile
```

```
Ser Cys Lys Ala Arg Phe Gly Phe Glu Arg Val Phe Asn Pro Val Ile
        275                 280                 285 aaa tgg tac atc aaa gat tct gac cta gag tgg gaa gtc tca gta cct    1392
Lys Trp Tyr Ile Lys Asp Ser Asp Leu Glu Trp Glu Val Ser Val Pro
        290                 295                 300 gag gcg aaa agt att aaa tcc act tta aag gat gaa atc att gag cgt    1440
Glu Ala Lys Ser Ile Lys Ser Thr Leu Lys Asp Glu Ile Ile Glu Arg
305                 310                 315 aat atc atc ttg gaa aaa gtc act cag cgt gat ctt cgc agg aag ttt    1488
Asn Ile Ile Leu Glu Lys Val Thr Gln Arg Asp Leu Arg Arg Lys Phe
320                 325                 330                 335 gtt tgc ttt gtc cag aac tcc att gga aac aca acc cag tcc gtc caa    1536
Val Cys Phe Val Gln Asn Ser Ile Gly Asn Thr Thr Gln Ser Val Gln
            340                 345                 350 ctg aaa gaa aag aga gga gtg gtg ctc ctg tac atc ctg ctt ggc acc    1584
Leu Lys Glu Lys Arg Gly Val Val Leu Leu Tyr Ile Leu Leu Gly Thr
        355                 360                 365 atc ggg acc ctg gtg gcc gtg ctg gcg gcg agt gcc ctc ctc tac agg    1632
Ile Gly Thr Leu Val Ala Val Leu Ala Ala Ser Ala Leu Leu Tyr Arg
        370                 375                 380 cac tgg att gaa ata gtg ctg ctg tac cgg acc tac cag agc aag gat    1680
His Trp Ile Glu Ile Val Leu Leu Tyr Arg Thr Tyr Gln Ser Lys Asp
385                 390                 395 cag acg ctt ggg gat aaa aag gat ttt gat gct ttc gta tcc tat gca    1728
Gln Thr Leu Gly Asp Lys Lys Asp Phe Asp Ala Phe Val Ser Tyr Ala
400                 405                 410                 415 aaa tgg agc tct ttt cca agt gag gcc act tca tct ctg agt gaa gaa    1776
Lys Trp Ser Ser Phe Pro Ser Glu Ala Thr Ser Ser Leu Ser Glu Glu
            420                 425                 430 cac ttg gcc ctg agc cta ttt cct gat gtt tta gaa aac aaa tat gga    1824
His Leu Ala Leu Ser Leu Phe Pro Asp Val Leu Glu Asn Lys Tyr Gly
        435                 440                 445 tat agc ctg tgt ttg ctt gaa aga gat gtg gct cca gga gga gtg tat    1872
Tyr Ser Leu Cys Leu Leu Glu Arg Asp Val Ala Pro Gly Gly Val Tyr
        450                 455                 460 gca gaa gac att gtg agc att att aag aga agc aga aga gga ata ttt    1920
Ala Glu Asp Ile Val Ser Ile Ile Lys Arg Ser Arg Arg Gly Ile Phe
465                 470                 475 atc ttg agc ccc aac tat gtc aat gga ccc agt atc ttt gaa cta caa    1968
Ile Leu Ser Pro Asn Tyr Val Asn Gly Pro Ser Ile Phe Glu Leu Gln
480                 485                 490                 495 gca gca gtg aat ctt gcc ttg gat gat caa aca ctg aaa ctc att tta    2016
Ala Ala Val Asn Leu Ala Leu Asp Asp Gln Thr Leu Lys Leu Ile Leu
            500                 505                 510 att aag ttc tgt tac ttc caa gag cca gag tct cta cct cat ctc gtg    2064
Ile Lys Phe Cys Tyr Phe Gln Glu Pro Glu Ser Leu Pro His Leu Val
        515                 520                 525 aaa aaa gct ctc agg gtt ttg ccc aca gtt act tgg aga ggc tta aaa    2112
Lys Lys Ala Leu Arg Val Leu Pro Thr Val Thr Trp Arg Gly Leu Lys
        530                 535                 540 tca gtt cct ccc aat tct agg ttc tgg gcc aaa atg cgc tac cac atg    2160
Ser Val Pro Pro Asn Ser Arg Phe Trp Ala Lys Met Arg Tyr His Met
545                 550                 555 cct gtg aaa aac tct cag gga ttc acg tgg aac cag ctc aga att acc    2208
Pro Val Lys Asn Ser Gln Gly Phe Thr Trp Asn Gln Leu Arg Ile Thr
560                 565                 570                 575 tct agg att ttt cag tgg aaa gga ctc agt aga aca gaa acc act ggg    2256
Ser Arg Ile Phe Gln Trp Lys Gly Leu Ser Arg Thr Glu Thr Thr Gly
            580                 585                 590
```

-continued

```
agg agc tcc cag cct aag gaa tgg tga aatgagccct ggagcccct         2303
Arg Ser Ser Gln Pro Lys Glu Trp
            595 ccagtccagt ccctgggata gagatgttgc tggacagaac tcacagctct gtgtgtgtgt  2363 gttcaggctg ataggaaatt caaagagtct cctgccagca ccaagcaagc ttgatggaca  2423 atggaatggg attgagactg tggtttagag cctttgattt cctggactgg acagacggcg  2483 agtgaattct ctagaccttg ggtactttca gtacacaaca cccctaagat ttcccagtgg  2543 tccgagcaga atcagaaaat acagctactt ctgccttatg gctagggaac tgtcatgtct  2603 accatgtatt gtacatatga ctttatgtat acttgcaatc aaataaatat tattttatta  2663 gaaaaaaaac cggaattc                                                2681
```

<210> SEQ ID NO 2
<211> LENGTH: 599
<212> TYPE: PRT
<213> ORGANISM: Human AcPL

<400> SEQUENCE: 2

```
Met Leu Cys Leu Gly Trp Ile Phe Leu Trp Leu Val Ala Gly Glu Arg
  1               5                  10                  15

Ile Lys Gly Phe Asn Ile Ser Gly Cys Ser Thr Lys Lys Leu Leu Trp
             20                  25                  30

Thr Tyr Ser Thr Arg Ser Glu Glu Phe Val Leu Phe Cys Asp Leu
         35                  40                  45

Pro Glu Pro Gln Lys Ser His Phe Cys His Arg Asn Arg Leu Ser Pro
     50                  55                  60

Lys Gln Val Pro Glu His Leu Pro Phe Met Gly Ser Asn Asp Leu Ser
 65                  70                  75                  80

Asp Val Gln Trp Tyr Gln Gln Pro Ser Asn Gly Asp Pro Leu Glu Asp
                 85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285
```

```
Trp Tyr Ile Lys Asp Ser Asp Leu Glu Trp Glu Val Ser Val Pro Glu
        290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
                340                 345                 350

Lys Glu Lys Arg Gly Val Val Leu Leu Tyr Ile Leu Leu Gly Thr Ile
            355                 360                 365

Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
                420                 425                 430

Leu Ala Leu Ser Leu Phe Pro Asp Val Leu Glu Asn Lys Tyr Gly Tyr
            435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
    515                 520                 525

Lys Ala Leu Arg Val Leu Pro Thr Val Thr Trp Arg Gly Leu Lys Ser
530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
                580                 585                 590

Ser Ser Gln Pro Lys Glu Trp
            595

<210> SEQ ID NO 3
<211> LENGTH: 1626
<212> TYPE: DNA
<213> ORGANISM: Human IL-1Rrp1
<220> FEATURE:
<221> NAME/KEY: CDS
<222> LOCATION: (1)..(1626)

<400> SEQUENCE: 3 atg aat tgt aga gaa tta ccc ttg acc ctt tgg gtg ctt ata tct gta      48
Met Asn Cys Arg Glu Leu Pro Leu Thr Leu Trp Val Leu Ile Ser Val
 1               5                  10                  15 agc act gca gaa tct tgt act tca cgt ccc cac att act gtg gtt gaa      96
Ser Thr Ala Glu Ser Cys Thr Ser Arg Pro His Ile Thr Val Val Glu
            20                  25                  30
```

-continued

| | | |
|---|---|---|
| ggg gaa cct ttc tat ctg aaa cat tgc tcg tgt tca ctt gca cat gag<br>Gly Glu Pro Phe Tyr Leu Lys His Cys Ser Cys Ser Leu Ala His Glu<br>35                   40                   45 | 144 |
| att gaa aca acc acc aaa agc tgg tac aaa agc agt gga tca cag gaa<br>Ile Glu Thr Thr Thr Lys Ser Trp Tyr Lys Ser Ser Gly Ser Gln Glu<br>50                     55                   60 | 192 |
| cat gtg gag ctg aac cca agg agt tcc tcg aga att gct ttg cat gat<br>His Val Glu Leu Asn Pro Arg Ser Ser Ser Arg Ile Ala Leu His Asp<br>65                   70                   75                   80 | 240 |
| tgt gtt ttg gag ttt tgg cca gtt gag ttg aat gac aca gga tct tac<br>Cys Val Leu Glu Phe Trp Pro Val Glu Leu Asn Asp Thr Gly Ser Tyr<br>                   85                   90                   95 | 288 |
| ttt ttc caa atg aaa aat tat act cag aaa tgg aaa tta aat gtc atc<br>Phe Phe Gln Met Lys Asn Tyr Thr Gln Lys Trp Lys Leu Asn Val Ile<br>           100                  105                 110 | 336 |
| aga aga aat aaa cac agc tgt ttc act gaa aga caa gta act agt aaa<br>Arg Arg Asn Lys His Ser Cys Phe Thr Glu Arg Gln Val Thr Ser Lys<br>           115                  120                 125 | 384 |
| att gtg gaa gtt aaa aaa ttt ttt cag ata acc tgt gaa aac agt tac<br>Ile Val Glu Val Lys Lys Phe Phe Gln Ile Thr Cys Glu Asn Ser Tyr<br>130                  135                 140 | 432 |
| tat caa aca ctg gtc aac agc aca tca ttg tat aag aac tgt aaa aag<br>Tyr Gln Thr Leu Val Asn Ser Thr Ser Leu Tyr Lys Asn Cys Lys Lys<br>145                  150                 155                 160 | 480 |
| cta cta ctg gag aac aat aaa aac cca acg ata aag aag aac gcc gag<br>Leu Leu Leu Glu Asn Asn Lys Asn Pro Thr Ile Lys Lys Asn Ala Glu<br>                   165                 170                 175 | 528 |
| ttt gaa gat cag ggg tat tac tcc tgc gtg cat ttc ctt cat cat aat<br>Phe Glu Asp Gln Gly Tyr Tyr Ser Cys Val His Phe Leu His His Asn<br>           180                  185                 190 | 576 |
| gga aaa cta ttt aat atc acc aaa acc ttc aat ata aca ata gtg gaa<br>Gly Lys Leu Phe Asn Ile Thr Lys Thr Phe Asn Ile Thr Ile Val Glu<br>           195                  200                 205 | 624 |
| gat cgc agt aat ata gtt ccg gtt ctt ctt gga cca aag ctt aac cat<br>Asp Arg Ser Asn Ile Val Pro Val Leu Leu Gly Pro Lys Leu Asn His<br>210                  215                 220 | 672 |
| gtt gca gtg gaa tta gga aaa aac gta agg ctc aac tgc tct gct ttg<br>Val Ala Val Glu Leu Gly Lys Asn Val Arg Leu Asn Cys Ser Ala Leu<br>225                  230                 235                 240 | 720 |
| ctg aat gaa gag gat gta att tat tgg atg ttt ggg gaa gaa aat gga<br>Leu Asn Glu Glu Asp Val Ile Tyr Trp Met Phe Gly Glu Glu Asn Gly<br>                   245                 250                 255 | 768 |
| tcg gat cct aat ata cat gaa gag aaa gaa atg aga att atg act cca<br>Ser Asp Pro Asn Ile His Glu Glu Lys Glu Met Arg Ile Met Thr Pro<br>           260                  265                 270 | 816 |
| gaa ggc aaa tgg cat gct tca aaa gta ttg aga att gaa aat att ggt<br>Glu Gly Lys Trp His Ala Ser Lys Val Leu Arg Ile Glu Asn Ile Gly<br>           275                  280                 285 | 864 |
| gaa agc aat cta aat gtt tta tat aat tgc act gtg gcc agc acg gga<br>Glu Ser Asn Leu Asn Val Leu Tyr Asn Cys Thr Val Ala Ser Thr Gly<br>290                  295                 300 | 912 |
| ggc aca gac acc aaa agc ttc atc ttg gtg aga aaa gca gac atg gct<br>Gly Thr Asp Thr Lys Ser Phe Ile Leu Val Arg Lys Ala Asp Met Ala<br>305                  310                 315                 320 | 960 |
| gat atc cca ggc cac gtc ttc aca aga gga atg atc ata gct gtt ttg<br>Asp Ile Pro Gly His Val Phe Thr Arg Gly Met Ile Ile Ala Val Leu<br>                   325                 330                 335 | 1008 |
| atc ttg gtg gca gta gtg tgc cta gtg act gtg tgt gtc att tat aga<br>Ile Leu Val Ala Val Val Cys Leu Val Thr Val Cys Val Ile Tyr Arg | 1056 |

-continued

```
                   340                 345                 350
gtt gac ttg gtt cta ttt tat aga cat tta acg aga aga gat gaa aca      1104
Val Asp Leu Val Leu Phe Tyr Arg His Leu Thr Arg Arg Asp Glu Thr
        355                 360                 365 tta aca gat gga aaa aca tat gat gct ttt gtg tct tac cta aaa gaa      1152
Leu Thr Asp Gly Lys Thr Tyr Asp Ala Phe Val Ser Tyr Leu Lys Glu
    370                 375                 380 tgc cga cct gaa aat gga gag gag cac acc ttt gct gtg gag att ttg      1200
Cys Arg Pro Glu Asn Gly Glu Glu His Thr Phe Ala Val Glu Ile Leu
385                 390                 395                 400 ccc agg gtg ttg gag aaa cat ttt ggg tat aag tta tgc ata ttt gaa      1248
Pro Arg Val Leu Glu Lys His Phe Gly Tyr Lys Leu Cys Ile Phe Glu
                405                 410                 415 agg gat gta gtg cct gga gga gct gtt gtt gat gaa atc cac tca ctg      1296
Arg Asp Val Val Pro Gly Gly Ala Val Val Asp Glu Ile His Ser Leu
            420                 425                 430 ata gag aaa agc cga aga cta atc att gtc cta agt aaa agt tat atg      1344
Ile Glu Lys Ser Arg Arg Leu Ile Ile Val Leu Ser Lys Ser Tyr Met
        435                 440                 445 tct aat gag gtc agg tat gaa ctt gaa agt gga ctc cat gaa gca ttg      1392
Ser Asn Glu Val Arg Tyr Glu Leu Glu Ser Gly Leu His Glu Ala Leu
    450                 455                 460 gtg gaa aga aaa att aaa ata atc tta att gaa ttt aca cct gtt act      1440
Val Glu Arg Lys Ile Lys Ile Ile Leu Ile Glu Phe Thr Pro Val Thr
465                 470                 475                 480 gac ttc aca ttc ttg ccc caa tca cta aag ctt ttg aaa tct cac aga      1488
Asp Phe Thr Phe Leu Pro Gln Ser Leu Lys Leu Leu Lys Ser His Arg
                485                 490                 495 gtt ctg aag tgg aag gcc gat aaa tct ctt tct tat aac tca agg ttc      1536
Val Leu Lys Trp Lys Ala Asp Lys Ser Leu Ser Tyr Asn Ser Arg Phe
            500                 505                 510 tgg aag aac ctt ctt tac tta atg cct gca aaa aca gtc aag cca ggt      1584
Trp Lys Asn Leu Leu Tyr Leu Met Pro Ala Lys Thr Val Lys Pro Gly
        515                 520                 525 aga gac gaa ccg gaa gtc ttg cct gtt ctt tcc gag tct taa              1626
Arg Asp Glu Pro Glu Val Leu Pro Val Leu Ser Glu Ser
    530                 535                 540
```

<210> SEQ ID NO 4
<211> LENGTH: 541
<212> TYPE: PRT
<213> ORGANISM: Human IL-1Rrp1

<400> SEQUENCE: 4

```
Met Asn Cys Arg Glu Leu Pro Leu Thr Leu Trp Val Leu Ile Ser Val
 1               5                  10                  15

Ser Thr Ala Glu Ser Cys Thr Ser Arg Pro His Ile Thr Val Val Glu
             20                  25                  30

Gly Glu Pro Phe Tyr Leu Lys His Cys Ser Cys Ser Leu Ala His Glu
         35                  40                  45

Ile Glu Thr Thr Thr Lys Ser Trp Tyr Lys Ser Ser Gly Ser Gln Glu
     50                  55                  60

His Val Glu Leu Asn Pro Arg Ser Ser Arg Ile Ala Leu His Asp
 65                  70                  75                  80

Cys Val Leu Glu Phe Trp Pro Val Glu Leu Asn Asp Thr Gly Ser Tyr
             85                  90                  95

Phe Phe Gln Met Lys Asn Tyr Thr Gln Lys Trp Lys Leu Asn Val Ile
        100                 105                 110
```

-continued

```
Arg Arg Asn Lys His Ser Cys Phe Thr Glu Arg Gln Val Thr Ser Lys
        115                 120                 125
Ile Val Glu Val Lys Lys Phe Phe Gln Ile Thr Cys Glu Asn Ser Tyr
    130                 135                 140
Tyr Gln Thr Leu Val Asn Ser Thr Ser Leu Tyr Lys Asn Cys Lys Lys
145                 150                 155                 160
Leu Leu Leu Glu Asn Asn Lys Asn Pro Thr Ile Lys Lys Asn Ala Glu
                165                 170                 175
Phe Glu Asp Gln Gly Tyr Tyr Ser Cys Val His Phe Leu His His Asn
            180                 185                 190
Gly Lys Leu Phe Asn Ile Thr Lys Thr Phe Asn Ile Thr Ile Val Glu
        195                 200                 205
Asp Arg Ser Asn Ile Val Pro Val Leu Leu Gly Pro Lys Leu Asn His
    210                 215                 220
Val Ala Val Glu Leu Gly Lys Asn Val Arg Leu Asn Cys Ser Ala Leu
225                 230                 235                 240
Leu Asn Glu Glu Asp Val Ile Tyr Trp Met Phe Gly Glu Glu Asn Gly
                245                 250                 255
Ser Asp Pro Asn Ile His Glu Glu Lys Glu Met Arg Ile Met Thr Pro
            260                 265                 270
Glu Gly Lys Trp His Ala Ser Lys Val Leu Arg Ile Glu Asn Ile Gly
        275                 280                 285
Glu Ser Asn Leu Asn Val Leu Tyr Asn Cys Thr Val Ala Ser Thr Gly
    290                 295                 300
Gly Thr Asp Thr Lys Ser Phe Ile Leu Val Arg Lys Ala Asp Met Ala
305                 310                 315                 320
Asp Ile Pro Gly His Val Phe Thr Arg Gly Met Ile Ile Ala Val Leu
                325                 330                 335
Ile Leu Val Ala Val Val Cys Leu Val Thr Val Cys Val Ile Tyr Arg
            340                 345                 350
Val Asp Leu Val Leu Phe Tyr Arg His Leu Thr Arg Arg Asp Glu Thr
        355                 360                 365
Leu Thr Asp Gly Lys Thr Tyr Asp Ala Phe Val Ser Tyr Leu Lys Glu
    370                 375                 380
Cys Arg Pro Glu Asn Gly Glu Glu His Thr Phe Ala Val Glu Ile Leu
385                 390                 395                 400
Pro Arg Val Leu Glu Lys His Phe Gly Tyr Lys Leu Cys Ile Phe Glu
                405                 410                 415
Arg Asp Val Val Pro Gly Gly Ala Val Val Asp Glu Ile His Ser Leu
            420                 425                 430
Ile Glu Lys Ser Arg Arg Leu Ile Ile Val Leu Ser Lys Ser Tyr Met
        435                 440                 445
Ser Asn Glu Val Arg Tyr Glu Leu Glu Ser Gly Leu His Glu Ala Leu
    450                 455                 460
Val Glu Arg Lys Ile Lys Ile Ile Leu Ile Glu Phe Thr Pro Val Thr
465                 470                 475                 480
Asp Phe Thr Phe Leu Pro Gln Ser Leu Lys Leu Leu Lys Ser His Arg
                485                 490                 495
Val Leu Lys Trp Lys Ala Asp Lys Ser Leu Ser Tyr Asn Ser Arg Phe
            500                 505                 510
Trp Lys Asn Leu Leu Tyr Leu Met Pro Ala Lys Thr Val Lys Pro Gly
        515                 520                 525
Arg Asp Glu Pro Glu Val Leu Pro Val Leu Ser Glu Ser
```

<210> SEQ ID NO 5
<211> LENGTH: 2481
<212> TYPE: DNA
<213> ORGANISM: Murine AcPL
<220> FEATURE:
<221> NAME/KEY: CDS
<222> LOCATION: (428)..(2272)

<400> SEQUENCE: 5

| | |
|---|---|
| gcaggcttac tcaccatttc aactaaacct aaccacaacc cctttcttgt caaggaggct | 60 |
| ggccagagga cagctttgaa tgctttattt caggagtttt cttccgtgga taaagatgca | 120 |
| caagctggca ttcactgaca taaagacttg aatttcttta tttgttgtgt atgtaagagc | 180 |
| aggaaacaaa ggaaagagac cttgcagatc ttcagatcat ctcaccggcc tccgacctcc | 240 |
| ttctgtagag aaggcgaata gtggtggcaa gatgagaaac tttgaaaccc tcttcctcca | 300 |
| gatatgattc tcccttctac tactgaacag aagtgaagag gatgccagag aaagaggttt | 360 |
| gcctctctgc actctccaca ctggcgatca gaagtagctg aagccatgac aggagcaaag | 420 |

| | | |
|---|---|---|
| gggaacc atg ctc tgt ttg ggc tgg gtg ttt ctt tgg ttt gtt gca gga | | 469 |
| Met Leu Cys Leu Gly Trp Val Phe Leu Trp Phe Val Ala Gly | | |
| 1               5                   10 | | |
| gag aag acc aca gga ttt aat cat tca gct tgt gcc acc aaa aaa ctt | | 517 |
| Glu Lys Thr Thr Gly Phe Asn His Ser Ala Cys Ala Thr Lys Lys Leu | | |
| 15                  20                  25                  30 | | |
| ctg tgg aca tat tct gca agg ggt gca gag aat ttt gtc cta ttt tgt | | 565 |
| Leu Trp Thr Tyr Ser Ala Arg Gly Ala Glu Asn Phe Val Leu Phe Cys | | |
|                    35                  40                  45 | | |
| gac tta caa gag ctt cag gag caa aaa ttc tcc cat gca agt caa ctg | | 613 |
| Asp Leu Gln Glu Leu Gln Glu Gln Lys Phe Ser His Ala Ser Gln Leu | | |
|                50                  55                  60 | | |
| tca cca aca caa agt cct gct cac aaa cct tgc agt ggc agt cag aag | | 661 |
| Ser Pro Thr Gln Ser Pro Ala His Lys Pro Cys Ser Gly Ser Gln Lys | | |
|            65                  70                  75 | | |
| gac cta tct gat gtc cag tgg tac atg caa cct cgg agt gga agt cca | | 709 |
| Asp Leu Ser Asp Val Gln Trp Tyr Met Gln Pro Arg Ser Gly Ser Pro | | |
|        80                  85                  90 | | |
| cta gag gag atc agt aga aac tct ccc cat atg cag agt gaa ggc atg | | 757 |
| Leu Glu Glu Ile Ser Arg Asn Ser Pro His Met Gln Ser Glu Gly Met | | |
|    95                  100                 105                 110 | | |
| ctg cat ata ttg gcc cca cag acg aac agc att tgg tca tat att tgt | | 805 |
| Leu His Ile Leu Ala Pro Gln Thr Asn Ser Ile Trp Ser Tyr Ile Cys | | |
|                    115                 120                 125 | | |
| aga ccc aga att agg agc ccc cag gat atg gcc tgt tgt atc aag aca | | 853 |
| Arg Pro Arg Ile Arg Ser Pro Gln Asp Met Ala Cys Cys Ile Lys Thr | | |
|                130                 135                 140 | | |
| gtc tta gaa gtt aag cct cag aga aac gtg tcc tgt ggg aac aca gca | | 901 |
| Val Leu Glu Val Lys Pro Gln Arg Asn Val Ser Cys Gly Asn Thr Ala | | |
|            145                 150                 155 | | |
| caa gat gaa caa gtc cta ctt ctt ggc agt act ggc tcc att cat tgt | | 949 |
| Gln Asp Glu Gln Val Leu Leu Leu Gly Ser Thr Gly Ser Ile His Cys | | |
|        160                 165                 170 | | |
| ccc agt ctc agc tgc caa agt gat gta cag agt cca gag atg acc tgg | | 997 |
| Pro Ser Leu Ser Cys Gln Ser Asp Val Gln Ser Pro Glu Met Thr Trp | | |
| 175                 180                 185                 190 | | |
| tac aag gat gga aga cta ctt cct gag cac aag aaa aat cca att gag | | 1045 |
| Tyr Lys Asp Gly Arg Leu Leu Pro Glu His Lys Lys Asn Pro Ile Glu | | |
|                    195                 200                 205 | | |

-continued

```
atg gca gat att tat gtt ttt aat caa ggc ttg tat gta tgt gat tac    1093
Met Ala Asp Ile Tyr Val Phe Asn Gln Gly Leu Tyr Val Cys Asp Tyr
        210                 215                 220 aca cag tca gat aat gtg agt tcc tgg aca gtc cga gct gtg gtt aaa    1141
Thr Gln Ser Asp Asn Val Ser Ser Trp Thr Val Arg Ala Val Val Lys
225                 230                 235 gtg aga acc att ggt aag gac atc aat gtg aag ccg gaa att ctg gat    1189
Val Arg Thr Ile Gly Lys Asp Ile Asn Val Lys Pro Glu Ile Leu Asp
        240                 245                 250 ccc att aca gat aca ctg gac gta gag ctt gga aag cct tta act ctc    1237
Pro Ile Thr Asp Thr Leu Asp Val Glu Leu Gly Lys Pro Leu Thr Leu
255                 260                 265                 270 ccc tgc aga gta cag ttt ggc ttc caa aga ctt tca aag cct gta ata    1285
Pro Cys Arg Val Gln Phe Gly Phe Gln Arg Leu Ser Lys Pro Val Ile
                275                 280                 285 aag tgg tat gtc aaa gaa tct aca cag gag tgg gaa atg tca gta ttt    1333
Lys Trp Tyr Val Lys Glu Ser Thr Gln Glu Trp Glu Met Ser Val Phe
            290                 295                 300 gag gag aaa aga att caa tcc act ttc aag aat gaa gtc att gaa cgt    1381
Glu Glu Lys Arg Ile Gln Ser Thr Phe Lys Asn Glu Val Ile Glu Arg
        305                 310                 315 acc atc ttc ttg aga gaa gtt acc cag aga gat ctc agc aga aag ttt    1429
Thr Ile Phe Leu Arg Glu Val Thr Gln Arg Asp Leu Ser Arg Lys Phe
    320                 325                 330 gtt tgc ttt gcc cag aac tcc att ggg aac aca aca cgg acc ata cgg    1477
Val Cys Phe Ala Gln Asn Ser Ile Gly Asn Thr Thr Arg Thr Ile Arg
335                 340                 345                 350 ctg agg aag aag gaa gag gtg gtg ttt gta tac atc ctc ctc ggc acg    1525
Leu Arg Lys Lys Glu Glu Val Val Phe Val Tyr Ile Leu Leu Gly Thr
                355                 360                 365 gcc ttg atg ctg gtg ggc gtt ctg gtg gca gct gct ttc ctc tac tgg    1573
Ala Leu Met Leu Val Gly Val Leu Val Ala Ala Ala Phe Leu Tyr Trp
            370                 375                 380 tac tgg att gaa gtt gtc ctg ctc tgt cga acc tac aag aac aaa gat    1621
Tyr Trp Ile Glu Val Val Leu Leu Cys Arg Thr Tyr Lys Asn Lys Asp
        385                 390                 395 gag act ctg ggg gat aag aag gaa ttc gat gca ttt gta tcc tac tcg    1669
Glu Thr Leu Gly Asp Lys Lys Glu Phe Asp Ala Phe Val Ser Tyr Ser
    400                 405                 410 aat tgg agc tct cct gag act gac gcc gtg gga tct ctg agt gag gaa    1717
Asn Trp Ser Ser Pro Glu Thr Asp Ala Val Gly Ser Leu Ser Glu Glu
415                 420                 425                 430 cac ctg gct ctg aat ctt ttc ccg gaa gtg cta gaa gac acc tat ggg    1765
His Leu Ala Leu Asn Leu Phe Pro Glu Val Leu Glu Asp Thr Tyr Gly
                435                 440                 445 tac aga ttg tgt ttg ctt gac cga gat gtg acc cca gga gga gtg tat    1813
Tyr Arg Leu Cys Leu Leu Asp Arg Asp Val Thr Pro Gly Gly Val Tyr
            450                 455                 460 gca gat gac att gtg agc atc att aag aaa agc cga aga gga ata ttt    1861
Ala Asp Asp Ile Val Ser Ile Ile Lys Lys Ser Arg Arg Gly Ile Phe
        465                 470                 475 atc ctg agt ccc agc tac ctc aat gga ccc cgt gtc ttt gag cta caa    1909
Ile Leu Ser Pro Ser Tyr Leu Asn Gly Pro Arg Val Phe Glu Leu Gln
    480                 485                 490 gca gca gtg aat ctt gcc ttg gtt gat cag aca ctg aag ttg att tta    1957
Ala Ala Val Asn Leu Ala Leu Val Asp Gln Thr Leu Lys Leu Ile Leu
495                 500                 505                 510 att aag ttc tgt tcc ttc caa gag cca gaa tct ctt cct tac ctt gtc    2005
Ile Lys Phe Cys Ser Phe Gln Glu Pro Glu Ser Leu Pro Tyr Leu Val
                515                 520                 525
```

| | | | | | | | | | | | | | | | |
|---|---|---|---|---|---|---|---|---|---|---|---|---|---|---|---|
| aaa | aag | gct | ctg | cgg | gtt | ctc | ccc | aca | gtc | aca | tgg | aaa | ggc | ttg | aag | 2053 |
| Lys | Lys | Ala | Leu | Arg | Val | Leu | Pro | Thr | Val | Thr | Trp | Lys | Gly | Leu | Lys | |
| | | | 530 | | | | | 535 | | | | | 540 | | | |

| tcg | gtc | cac | gcc | agt | tcc | agg | ttc | tgg | acc | caa | att | cgt | tac | cac | atg | 2101 |
| Ser | Val | His | Ala | Ser | Ser | Arg | Phe | Trp | Thr | Gln | Ile | Arg | Tyr | His | Met | |
| | | 545 | | | | | 550 | | | | | 555 | | | | |

| cct | gtg | aag | aac | tcc | aac | agg | ttt | atg | ttc | aac | ggg | ctc | aga | att | ttc | 2149 |
| Pro | Val | Lys | Asn | Ser | Asn | Arg | Phe | Met | Phe | Asn | Gly | Leu | Arg | Ile | Phe | |
| 560 | | | | | 565 | | | | | 570 | | | | | | |

| ctg | aag | ggc | ttt | tcc | cct | gaa | aag | gac | cta | gtg | aca | cag | aaa | ccc | ctg | 2197 |
| Leu | Lys | Gly | Phe | Ser | Pro | Glu | Lys | Asp | Leu | Val | Thr | Gln | Lys | Pro | Leu | |
| 575 | | | | | 580 | | | | | 585 | | | | | 590 | |

| gaa | gga | atg | ccc | aag | tct | ggg | aat | gac | cac | gga | gct | cag | aac | ctc | ctt | 2245 |
| Glu | Gly | Met | Pro | Lys | Ser | Gly | Asn | Asp | His | Gly | Ala | Gln | Asn | Leu | Leu | |
| | | | | 595 | | | | | 600 | | | | | 605 | | |

| ctc | tac | agt | gac | cag | aag | agg | tgc | tga | tgggtagaac | | ttgctgtgtg | | | | | 2292 |
| Leu | Tyr | Ser | Asp | Gln | Lys | Arg | Cys | | | | | | | | | |
| | | | | 610 | | | | | | | | | | | | | gatcaggctg atagaaattg agcctttctg ctctcagtgc caagcaagct tgacaggcag    2352 tggaatgaag cggcatctgt ggttttaggg tctgggttcc tggaacagac acagagcaat    2412 actccagacc tctgccgtgt gcttagcaca catttccctg agagttccca agtagcctga    2472 acagaatca    2481

<210> SEQ ID NO 6
<211> LENGTH: 614
<212> TYPE: PRT
<213> ORGANISM: Murine AcPL

<400> SEQUENCE: 6

Met Leu Cys Leu Gly Trp Val Phe Leu Trp Phe Val Ala Gly Glu Lys
 1               5                  10                  15

Thr Thr Gly Phe Asn His Ser Ala Cys Ala Thr Lys Lys Leu Leu Trp
            20                  25                  30

Thr Tyr Ser Ala Arg Gly Ala Glu Asn Phe Val Leu Phe Cys Asp Leu
        35                  40                  45

Gln Glu Leu Gln Glu Gln Lys Phe Ser His Ala Ser Gln Leu Ser Pro
    50                  55                  60

Thr Gln Ser Pro Ala His Lys Pro Cys Ser Gly Ser Gln Lys Asp Leu
65                  70                  75                  80

Ser Asp Val Gln Trp Tyr Met Gln Pro Arg Ser Gly Ser Pro Leu Glu
                85                  90                  95

Glu Ile Ser Arg Asn Ser Pro His Met Gln Ser Glu Gly Met Leu His
            100                 105                 110

Ile Leu Ala Pro Gln Thr Asn Ser Ile Trp Ser Tyr Ile Cys Arg Pro
        115                 120                 125

Arg Ile Arg Ser Pro Gln Asp Met Ala Cys Cys Ile Lys Thr Val Leu
    130                 135                 140

Glu Val Lys Pro Gln Arg Asn Val Ser Cys Gly Asn Thr Ala Gln Asp
145                 150                 155                 160

Glu Gln Val Leu Leu Leu Gly Ser Thr Gly Ser Ile His Cys Pro Ser
                165                 170                 175

Leu Ser Cys Gln Ser Asp Val Gln Ser Pro Glu Met Thr Trp Tyr Lys
            180                 185                 190

Asp Gly Arg Leu Leu Pro Glu His Lys Lys Asn Pro Ile Glu Met Ala
        195                 200                 205

-continued

```
Asp Ile Tyr Val Phe Asn Gln Gly Leu Tyr Val Cys Asp Tyr Thr Gln
    210                 215                 220

Ser Asp Asn Val Ser Ser Trp Thr Val Arg Ala Val Lys Val Arg
225                 230                 235                 240

Thr Ile Gly Lys Asp Ile Asn Val Lys Pro Glu Ile Leu Asp Pro Ile
                245                 250                 255

Thr Asp Thr Leu Asp Val Glu Leu Gly Lys Pro Leu Thr Leu Pro Cys
            260                 265                 270

Arg Val Gln Phe Gly Phe Gln Arg Leu Ser Lys Pro Val Ile Lys Trp
        275                 280                 285

Tyr Val Lys Glu Ser Thr Gln Glu Trp Glu Met Ser Val Phe Glu Glu
    290                 295                 300

Lys Arg Ile Gln Ser Thr Phe Lys Asn Glu Val Ile Glu Arg Thr Ile
305                 310                 315                 320

Phe Leu Arg Glu Val Thr Gln Arg Asp Leu Ser Arg Lys Phe Val Cys
                325                 330                 335

Phe Ala Gln Asn Ser Ile Gly Asn Thr Thr Arg Thr Ile Arg Leu Arg
            340                 345                 350

Lys Lys Glu Glu Val Val Phe Val Tyr Ile Leu Leu Gly Thr Ala Leu
        355                 360                 365

Met Leu Val Gly Val Leu Ala Ala Ala Phe Leu Tyr Trp Tyr Trp
    370                 375                 380

Ile Glu Val Val Leu Leu Cys Arg Thr Tyr Lys Asn Lys Asp Glu Thr
385                 390                 395                 400

Leu Gly Asp Lys Lys Glu Phe Asp Ala Phe Val Ser Tyr Ser Asn Trp
                405                 410                 415

Ser Ser Pro Glu Thr Asp Ala Val Gly Ser Leu Ser Glu Glu His Leu
            420                 425                 430

Ala Leu Asn Leu Phe Pro Glu Val Leu Glu Asp Thr Tyr Gly Tyr Arg
        435                 440                 445

Leu Cys Leu Leu Asp Arg Asp Val Thr Pro Gly Gly Val Tyr Ala Asp
    450                 455                 460

Asp Ile Val Ser Ile Ile Lys Lys Ser Arg Arg Gly Ile Phe Ile Leu
465                 470                 475                 480

Ser Pro Ser Tyr Leu Asn Gly Pro Arg Val Phe Glu Leu Gln Ala Ala
                485                 490                 495

Val Asn Leu Ala Leu Val Asp Gln Thr Leu Lys Leu Ile Leu Ile Lys
            500                 505                 510

Phe Cys Ser Phe Gln Glu Pro Glu Ser Leu Pro Tyr Leu Val Lys Lys
        515                 520                 525

Ala Leu Arg Val Leu Pro Thr Val Thr Trp Lys Gly Leu Lys Ser Val
    530                 535                 540

His Ala Ser Ser Arg Phe Trp Thr Gln Ile Arg Tyr His Met Pro Val
545                 550                 555                 560

Lys Asn Ser Asn Arg Phe Met Phe Asn Gly Leu Arg Ile Phe Leu Lys
                565                 570                 575

Gly Phe Ser Pro Glu Lys Asp Leu Val Thr Gln Lys Pro Leu Glu Gly
            580                 585                 590

Met Pro Lys Ser Gly Asn Asp His Gly Ala Gln Asn Leu Leu Leu Tyr
        595                 600                 605

Ser Asp Gln Lys Arg Cys
    610
```

<210> SEQ ID NO 7
<211> LENGTH: 2830
<212> TYPE: DNA
<213> ORGANISM: Murine IL-1Rrp1
<220> FEATURE:
<221> NAME/KEY: CDS
<222> LOCATION: (381)..(1994)

<400> SEQUENCE: 7

```
tcccagccct ccacctccct accccggtc gttggcttct tcttcttctt cttctttttt        60
ttttttcctg cgataattct ctggtttgcc aaatctctct aatcaagctc ctggccttgc       120
ctcactgtgc cttccctccc tgtctgttgt cacagttgtg gaccaggagg tatttagtct       180
cacttgctgg gcgaatcctg cttcacagat gtaagcgaag gagaagccac tgcccaggcc       240
tgtgtgtggg ccacctctct gaaggtaagg gcagactctg atgtccagtc ctcactgtct       300
tctgctgtct ggagcaagga gaggaaccac ccacaacgat cctgaaaaca agagatacca       360
ttcaaagtgg aagcctaaac atg cat cat gaa gaa tta atc ttg aca ctc tgc       413
                     Met His His Glu Glu Leu Ile Leu Thr Leu Cys
                      1               5                   10 att ctc att gtt aaa agt gcc tca aaa agt tgt att cac cga tca caa         461
Ile Leu Ile Val Lys Ser Ala Ser Lys Ser Cys Ile His Arg Ser Gln
            15                  20                  25 att cat gtg gta gag gga gaa cct ttt tat ctg aag cca tgt ggc ata         509
Ile His Val Val Glu Gly Glu Pro Phe Tyr Leu Lys Pro Cys Gly Ile
         30                  35                  40 tct gca cca gtg cac agg aat gaa aca gcc acc atg aga tgg ttc aaa         557
Ser Ala Pro Val His Arg Asn Glu Thr Ala Thr Met Arg Trp Phe Lys
     45                  50                  55 ggc agt gct tca cat gag tat aga gag ctg aac aac aga agc tcg ccc         605
Gly Ser Ala Ser His Glu Tyr Arg Glu Leu Asn Asn Arg Ser Ser Pro
 60                  65                  70                  75 aga gtc act ttt cat gat cac acc ttg gaa ttc tgg cca gtt gag atg         653
Arg Val Thr Phe His Asp His Thr Leu Glu Phe Trp Pro Val Glu Met
                 80                  85                  90 gag gat gag gga acg tac att tct caa gtc gga aat gat cgt cgc aat         701
Glu Asp Glu Gly Thr Tyr Ile Ser Gln Val Gly Asn Asp Arg Arg Asn
             95                 100                 105 tgg acc tta aat gtc acc aaa aga aac aaa cac agc tgt ttc tct gac         749
Trp Thr Leu Asn Val Thr Lys Arg Asn Lys His Ser Cys Phe Ser Asp
         110                 115                 120 aag ctc gtg aca agc aga gat gtt gaa gtt aac aaa tct ctg cat atc         797
Lys Leu Val Thr Ser Arg Asp Val Glu Val Asn Lys Ser Leu His Ile
     125                 130                 135 act tgt aag aat cct aac tat gaa gag ctg atc cag gac aca tgg ctg         845
Thr Cys Lys Asn Pro Asn Tyr Glu Glu Leu Ile Gln Asp Thr Trp Leu
140                 145                 150                 155 tat aag aac tgt aag gaa ata tcc aaa acc cca agg atc ctg aag gat         893
Tyr Lys Asn Cys Lys Glu Ile Ser Lys Thr Pro Arg Ile Leu Lys Asp
                 160                 165                 170 gcc gag ttt gga gat gag ggc tac tac tcc tgc gtg ttt tct gtc cac         941
Ala Glu Phe Gly Asp Glu Gly Tyr Tyr Ser Cys Val Phe Ser Val His
             175                 180                 185 cat aat ggg aca cgg tac aac atc acc aag act gtc aat ata aca gtt         989
His Asn Gly Thr Arg Tyr Asn Ile Thr Lys Thr Val Asn Ile Thr Val
         190                 195                 200 att gaa gga agg agt aaa gta act cca gct att tta gga cca aag tgt        1037
Ile Glu Gly Arg Ser Lys Val Thr Pro Ala Ile Leu Gly Pro Lys Cys
     205                 210                 215
```

-continued

```
gag aag gtt ggt gta gaa cta gga aag gat gtg gag ttg aac tgc agt    1085
Glu Lys Val Gly Val Glu Leu Gly Lys Asp Val Glu Leu Asn Cys Ser
220                 225                 230                 235 gct tca ttg aat aaa gac gat ctg ttt tat tgg agc atc agg aaa gag    1133
Ala Ser Leu Asn Lys Asp Asp Leu Phe Tyr Trp Ser Ile Arg Lys Glu
            240                 245                 250 gac agc tca gac cct aat gtg caa gaa gac agg aag gag acg aca aca    1181
Asp Ser Ser Asp Pro Asn Val Gln Glu Asp Arg Lys Glu Thr Thr Thr
        255                 260                 265 tgg att tct gaa ggc aaa ctg cat gct tca aaa ata ctg aga ttt cag    1229
Trp Ile Ser Glu Gly Lys Leu His Ala Ser Lys Ile Leu Arg Phe Gln
    270                 275                 280 aaa att act gaa aac tat ctc aat gtt tta tat aat tgc acc gtg gcc    1277
Lys Ile Thr Glu Asn Tyr Leu Asn Val Leu Tyr Asn Cys Thr Val Ala
285                 290                 295 aac gaa gaa gcc ata gac acc aag agc ttc gtc ttg gtg aga aaa gaa    1325
Asn Glu Glu Ala Ile Asp Thr Lys Ser Phe Val Leu Val Arg Lys Glu
300                 305                 310                 315 ata cct gat atc cca ggc cat gtc ttt aca gga gga gta act gtg ctt    1373
Ile Pro Asp Ile Pro Gly His Val Phe Thr Gly Gly Val Thr Val Leu
            320                 325                 330 gtt ctc gcc tct gtg gca gca gtg tgt ata gtg att ttg tgt gtc att    1421
Val Leu Ala Ser Val Ala Ala Val Cys Ile Val Ile Leu Cys Val Ile
        335                 340                 345 tat aaa gtt gac ttg gtt ctg ttc tat agg cgc ata gcg gaa aga gac    1469
Tyr Lys Val Asp Leu Val Leu Phe Tyr Arg Arg Ile Ala Glu Arg Asp
    350                 355                 360 gag aca cta aca gat ggt aaa aca tat gat gcc ttt gtg tct tac ctg    1517
Glu Thr Leu Thr Asp Gly Lys Thr Tyr Asp Ala Phe Val Ser Tyr Leu
365                 370                 375 aaa gag tgt cat cct gag aat aaa gaa gag tat act ttt gct gtg gag    1565
Lys Glu Cys His Pro Glu Asn Lys Glu Glu Tyr Thr Phe Ala Val Glu
380                 385                 390                 395 acg tta ccc agg gtc ctg gag aaa cag ttt ggg tat aag tta tgc ata    1613
Thr Leu Pro Arg Val Leu Glu Lys Gln Phe Gly Tyr Lys Leu Cys Ile
            400                 405                 410 ttt gaa aga gat gtg gtg cct ggc gga gct gtt gtc gag gag atc cat    1661
Phe Glu Arg Asp Val Val Pro Gly Gly Ala Val Val Glu Glu Ile His
        415                 420                 425 tca ctg ata gag aaa agc cgg agg cta atc atc gtt ctc agc cag agt    1709
Ser Leu Ile Glu Lys Ser Arg Arg Leu Ile Ile Val Leu Ser Gln Ser
    430                 435                 440 tac ctg act aac gga gcc agg cgt gag ctc gag agt gga ctc cac gaa    1757
Tyr Leu Thr Asn Gly Ala Arg Arg Glu Leu Glu Ser Gly Leu His Glu
445                 450                 455 gca ctg gta gag agg aag att aag atc atc tta att gag ttt act cca    1805
Ala Leu Val Glu Arg Lys Ile Lys Ile Ile Leu Ile Glu Phe Thr Pro
460                 465                 470                 475 gcc agc aac atc acc ttt ctc ccc ccg tcg ctg aaa ctc ctg aag tcc    1853
Ala Ser Asn Ile Thr Phe Leu Pro Pro Ser Leu Lys Leu Leu Lys Ser
            480                 485                 490 tac aga gtt cta aaa tgg agg gct gac agt ccc tcc atg aac tca agg    1901
Tyr Arg Val Leu Lys Trp Arg Ala Asp Ser Pro Ser Met Asn Ser Arg
        495                 500                 505 ttc tgg aag aat ctt gtt tac ctg atg ccc gca aaa gcc gtc aag cca    1949
Phe Trp Lys Asn Leu Val Tyr Leu Met Pro Ala Lys Ala Val Lys Pro
    510                 515                 520 tgg aga gag gag tcg gag gcg cgg tct gtt ctc tca gca cct tga       1994
Trp Arg Glu Glu Ser Glu Ala Arg Ser Val Leu Ser Ala Pro
525                 530                 535
```

-continued

```
gctccagacg agcttgatgt caaaagcaag tgaagcgctg ctagaggtca tgcgtgtgcc    2054
tattcacagc ggtagctgtg gttcaaaagg ctgaattttg tgactatacc ccccactccc    2114
agttaggaga gttgtcatcg ggtcatcaca gatgaaacag agccttggtt gtgatcctga    2174
actcgcagag ggggccttgg gattcacaag aaatcagttt gttattcttt cttcctctgg    2234
agcagtgatt cccaacctgt gggttgtggc ccctttggca aacctttatc tccaaaatag    2294
atgtacgcta tgattcataa ctgtagccaa ctcacagtta caaagtagca acgaaaaaag    2354
ttttatggtt gggggtttca ccacagtgtg aagaactgta ttaaagggtt gaagcattag    2414
gaaggttgag aaccgctggc ctagagctgt ctgcccaaag cttcttgtga ccttgcaagt    2474
gcctgagtga agcaagaata ttctagggaa gtctagagca gagactgtgc tgaacaaaca    2534
cagtagattt taggaaaacc aaaccaaacc aaatgaaagg aaaggaaaca gaaaaaaaaa    2594
caagaagaat ggggattctt aagtaatttt tgtaactcat gacttcatgt gctatttgac    2654
tgacttgaga aagaaggta aattcattca acatctgctg tcacaacagc tgtgtgtgaa     2714
aacctagcat cagaagagag ttgggagagt ttgagacttc gctttgttct tctatcagcc    2774
aagcttcgac acatgaagtt tattttatat gaaatatatt ttgtattaaa tctgcc        2830
```

<210> SEQ ID NO 8
<211> LENGTH: 537
<212> TYPE: PRT
<213> ORGANISM: Murine IL-1Rrp1

<400> SEQUENCE: 8

```
Met His His Glu Glu Leu Ile Leu Thr Leu Cys Ile Leu Ile Val Lys
  1               5                  10                  15

Ser Ala Ser Lys Ser Cys Ile His Arg Ser Gln Ile His Val Val Glu
             20                  25                  30

Gly Glu Pro Phe Tyr Leu Lys Pro Cys Gly Ile Ser Ala Pro Val His
         35                  40                  45

Arg Asn Glu Thr Ala Thr Met Arg Trp Phe Lys Gly Ser Ala Ser His
     50                  55                  60

Glu Tyr Arg Glu Leu Asn Asn Arg Ser Ser Pro Arg Val Thr Phe His
 65                  70                  75                  80

Asp His Thr Leu Glu Phe Trp Pro Val Glu Met Glu Asp Glu Gly Thr
                 85                  90                  95

Tyr Ile Ser Gln Val Gly Asn Asp Arg Arg Asn Trp Thr Leu Asn Val
            100                 105                 110

Thr Lys Arg Asn Lys His Ser Cys Phe Ser Asp Lys Leu Val Thr Ser
        115                 120                 125

Arg Asp Val Glu Val Asn Lys Ser Leu His Ile Thr Cys Lys Asn Pro
    130                 135                 140

Asn Tyr Glu Glu Leu Ile Gln Asp Thr Trp Leu Tyr Lys Asn Cys Lys
145                 150                 155                 160

Glu Ile Ser Lys Thr Pro Arg Ile Leu Lys Asp Ala Glu Phe Gly Asp
                165                 170                 175

Glu Gly Tyr Tyr Ser Cys Val Phe Ser Val His His Asn Gly Thr Arg
            180                 185                 190

Tyr Asn Ile Thr Lys Thr Val Asn Ile Thr Val Ile Glu Gly Arg Ser
        195                 200                 205

Lys Val Thr Pro Ala Ile Leu Gly Pro Lys Cys Glu Lys Val Gly Val
    210                 215                 220
```

-continued

```
Glu Leu Gly Lys Asp Val Glu Leu Asn Cys Ser Ala Ser Leu Asn Lys
225                 230                 235                 240

Asp Asp Leu Phe Tyr Trp Ser Ile Arg Lys Glu Asp Ser Ser Asp Pro
                245                 250                 255

Asn Val Gln Glu Asp Arg Lys Glu Thr Thr Thr Trp Ile Ser Glu Gly
            260                 265                 270

Lys Leu His Ala Ser Lys Ile Leu Arg Phe Gln Lys Ile Thr Glu Asn
            275                 280                 285

Tyr Leu Asn Val Leu Tyr Asn Cys Thr Val Ala Asn Glu Glu Ala Ile
        290                 295                 300

Asp Thr Lys Ser Phe Val Leu Val Arg Lys Glu Ile Pro Asp Ile Pro
305                 310                 315                 320

Gly His Val Phe Thr Gly Gly Val Thr Val Leu Val Leu Ala Ser Val
                325                 330                 335

Ala Ala Val Cys Ile Val Ile Leu Cys Val Ile Tyr Lys Val Asp Leu
            340                 345                 350

Val Leu Phe Tyr Arg Arg Ile Ala Glu Arg Asp Glu Thr Leu Thr Asp
        355                 360                 365

Gly Lys Thr Tyr Asp Ala Phe Val Ser Tyr Leu Lys Glu Cys His Pro
    370                 375                 380

Glu Asn Lys Glu Glu Tyr Thr Phe Ala Val Glu Thr Leu Pro Arg Val
385                 390                 395                 400

Leu Glu Lys Gln Phe Gly Tyr Lys Leu Cys Ile Phe Glu Arg Asp Val
                405                 410                 415

Val Pro Gly Gly Ala Val Val Glu Glu Ile His Ser Leu Ile Glu Lys
            420                 425                 430

Ser Arg Arg Leu Ile Ile Val Leu Ser Gln Ser Tyr Leu Thr Asn Gly
        435                 440                 445

Ala Arg Arg Glu Leu Glu Ser Gly Leu His Glu Ala Leu Val Glu Arg
    450                 455                 460

Lys Ile Lys Ile Ile Leu Ile Glu Phe Thr Pro Ala Ser Asn Ile Thr
465                 470                 475                 480

Phe Leu Pro Pro Ser Leu Lys Leu Leu Lys Ser Tyr Arg Val Leu Lys
                485                 490                 495

Trp Arg Ala Asp Ser Pro Ser Met Asn Ser Arg Phe Trp Lys Asn Leu
            500                 505                 510

Val Tyr Leu Met Pro Ala Lys Ala Val Lys Pro Trp Arg Glu Glu Ser
        515                 520                 525

Glu Ala Arg Ser Val Leu Ser Ala Pro
    530                 535
```

IL-18 RECEPTORS

CROSS-REFERENCE TO RELATED APPLICATIONS

This application is a divisional of application U.S. Ser. No. 10/439,458, filed May 15, 2003, and now issued as U.S. Pat. No. 7,169,581; which is a divisional of application U.S. Ser. No. 09/621,502, filed Jul. 21, 2000 and now issued as U.S. Pat. No. 6,589,764; which is a continuation of International Application number PCT/US99/01419, filed Jan. 22, 1999 and published in English on Jul. 29, 1999; which claims the benefit under 35 U.S.C. § 119(e) of U.S. Provisional Applications Ser. No. 60/072,301 filed Jan. 23, 1998; Ser. No. 60/078,835 filed Mar. 20, 1998; and Ser. No. 60/094,469 filed Jul. 28, 1998, all of which are incorporated by reference herein.

BACKGROUND OF THE INVENTION

1. Field of the Invention

The present invention relates to proteins that are members of the IL-1 receptor family. More particularly, the present invention relates to IL-1Rp1 and AcPL receptor complexes that mediate high affinity IL-18 binding and activity as well as inhibit IL-18 mediated activity.

2. Description of Related Art

The type I interleukin-1 receptor (IL-1RI) mediates the biological effects of interleukin-1, a pro-inflammatory cytokine (Sims et al., *Science* 241:585-589, 1988; Curtis et al., *Proc. Natl. Acad. Sci. USA* 86:3045-3049, 1989). A second interleukin-1 receptor (designated type II IL-1R or IL-1RII) binds IL-1, but does not appear to mediate signal transduction (McMahan et al., *EMBO J.* 10:2821, 1991; Sims et al., *Proc. Natl. Acad. Sci. USA* 90:6155-6159, 1993). IL-1RI and IL-1RII each bind IL-1□ and IL-1β. IL-1 has been implicated in chronic inflammatory diseases, such as rheumatoid arthritis and inflammatory bowel disease. There is increasing evidence that IL-1 plays a role in osteoporosis. All of these activities are initiated by the signaling function of the cytoplasmic portion of the Type I IL-1R. IL-1ra inhibits the activities of IL-1 by binding to the type I IL-1 receptor, thereby blocking access to IL-1α and IL-1β while eliciting no biological response of its own.

IL-1RI and IL-1RII belong to a family of proteins that exhibit significant sequence homology. One such protein is IL-1R accessory protein (IL-1R AcP), described in Greenfeder et al. (*J. Biol. Chem.* 270: 13757-13765, 1995). This protein, by itself, is not capable of binding IL-1, but does form a complex with IL-1RI and IL-1α and IL-1β. When co-expressed with IL-1RI, recombinant IL-1R AcP increases the binding affinity of IL-1RI for IL-1β (Greenfeder et al., supra).

Another protein exhibiting sequence homology to the IL-1RI and IL-1RII family is the IL-1 receptor related protein 1 (IL-1Rrp1) (See Parnet et al. *J. Biol Chem* 271:3967, 1996, and Torigoe et al., *J. Biol Chem* 272:25737, 1997). Still another such protein is AcPL.

IL-18 is a homologue of IL-1α and IL-1β and is known to activate many of the same responses activated by IL-1. For example, cells stimulated with IL-18 activate NFκB and produce known inflammatory mediators. IL-18 acts as a stimulator of Th1 cell growth and differentiation and is a potent inducer of γ-interferon production from Th1 cells. The Th1 class of helper T cells are known to mediate inflammatory reactions. IL-18 enhances NK cell killing activity and has been implicated in septic shock, liver destruction, inflammatory bowel disease and diabetes.

Recently it was shown that IL-1Rrp1 binds IL-18 and mediates IL-18 signaling in transfected cells. However, the IL-1Rrp1 binding affinity for IL-18 is very low and it is likely that one or more additional receptors or receptor subunits are involved with IL-18 binding and signaling.

Thus, the identification of additional receptors of for IL-18 is desirable. Such receptor proteins can be studied to determine whether or not they bind IL-18 and, if so, whether the receptors play a role in mediating signal transduction. Furthermore, soluble forms of such receptors may be used to inhibit IL-18 activity and ameliorate any inflammatory and/or autoimmune diseases attributable to IL-18 signaling. The possible existence of additional affinity-converting subunits for IL-18 can be explored, as well.

SUMMARY OF THE INVENTION

The present invention provides receptor polypeptides designated herein as IL-18 receptor complexes. More particularly, the present invention provides multimeric receptor polypeptides that include an AcPL polypeptide, or fragments thereof, and an IL-1Rrp1 polypeptide, or fragments thereof. The AcPL polypeptide may be covalently linked or noncovalently to the IL-1Rrp1 polypeptide by any suitable means. Such means include via a cross-linking reagent, a polypeptide linker, and associations such as via disulfide bonds or by use of leucine zippers. In one embodiment of the invention, the receptor is a fusion protein produced by recombinant DNA technology. This multimeric receptor of the present invention binds IL-18 with an affinity greater than that of IL-1Rrp1 alone. Disorders mediated by IL-18 may be treated by administering a therapeutically effective amount of this inventive receptor to a patient afflicted with such a disorder.

DETAILED DESCRIPTION OF THE INVENTION

The present invention is based upon the discovery that the coexpression of AcPL and IL-1Rrp1 results in a dramatic enhancement of NFκB activity in cells stimulated with IL-18. Because IL-1Rrp1 alone binds IL-18 only weakly and AcPL does not bind IL-18, the enhancement of NFκB activity by coexpressed AcPL and IL-1Rrp1 indicates that these polypeptides are subunits of an IL-18 receptor complex. In accordance with the present invention novel polypeptides, designated IL-18 receptor complexes, are provided. Advantageously, such dimeric IL-18 receptor complexes comprising IL-1Rrp1 and AcPL, or fragments thereof, are useful for inhibiting IL-18 activity, including the proinflammatory effects of IL-18, and can include IL-1Rrp1 and AcPL as proteins coexpressed in the same cell, or as IL-1Rrp1 linked to an AcPL as receptor subunits. Preferably the subunits are linked via covalent linkages. The subunits may be covalently linked by any suitable means, such as via a cross-linking reagent or a polypeptide linker.

In one embodiment of the present invention, the receptor is a fusion protein produced by recombinant DNA technology. Such fusion proteins can be prepared by transfecting cells with DNA encoding IL-1Rrp1:Fc fusion protein and DNA encoding AcPL:Fc fusion protein and coexpressing the dimers in the same cells.

Alternatively, AcPL/IL-1Rrp1 dimers can be prepared by fusing one of the receptor subunits to the constant region of an immunoglobulin heavy chain and fusing the other receptor subunit to the constant region of an immunoglobulin light chain. For example, an AcPL protein can be fused to the $CH_1$-hinge-$CH_2$—$CH_3$ region of human IgG1 and an IL-1Rrp1 protein can be fused to the C kappa region of the Ig kappa light chain, or vice versa. Cells transfected with DNA encoding the immunoglobulin light chain fusion protein and the immunoglobulin heavy chain fusion protein express heavy chain/light chain heterodimers containing the AcPL fusion protein and the IL-1Rrp1 fusion protein. Via disulfide linkages between the heavy chains, the heterodimers further combine to provide multimers, largely tetramers. Advantageously, in the event homodimers of two heavy or two light chain fusions are expressed, such homodimers can be separated easily from the heterodimers.

In addition to IL-18 receptor protein complexes, the present invention includes isolated DNA encoding heteromer polypeptides, expression vectors containing DNA encoding the heteromer polypeptides, and host cells transformed with such expression vectors. Methods for production of recombinant IL-18 receptor, including soluble forms of the protein, are also disclosed. Antibodies immunoreactive with the novel polypeptide are provided herein as well.

In one embodiment of the present invention, the polypeptide subunits of the heteromer IL-18 receptors include at least one AcPL subunit as described in SEQ ID NO:2 or SEQ ID NO: 6, and at least one IL-1Rrp1 subunit as described in SEQ ID NO:4 or SEQ ID NO:8. DNA encoding these polypeptide subunits are presented in SEQ ID NO:1, SEQ ID NO:5, SEQ ID NO:3 and SEQ ID NO:7, respectively. The AcPL subunit protein encoded by SEQ ID NO:1 includes an extracellular domain of 356 amino acids (residues 1-356 from N- to C-terminus of SEQ ID NO:2) that includes a signal peptide of 14 amino acids (residues 1-14 of SEQ ID NO:2); a transmembrane region of 25 amino acids (residues 357-381) and a cytoplasmic domain of 218 amino acids (residues 382-599). The AcPL subunit protein encoded by SEQ ID NO:5 includes an extracellular domain of 356 amino acids (residues 1-356 of SEQ ID NO:6) that includes a signal peptide of 14 amino acids (residues 1-14 of SEQ ID NO:6); a transmembrane region of 24 amino acids (residues 357-380) and a cytoplasmic domain of amino acid residues 381-614. The IL-1Rrp1 subunit protein encoded by SEQ ID NO:3 includes an extracellular domain of 329 amino acids (residues 1-329 of SEQ ID NO:4) that includes a signal peptide of 19 amino acids (residues 1-19 of SEQ ID NO:4); a transmembrane region of 21 amino acids (residues 330 to 350 of SEQ ID NO:4); and, a cytoplasmic domain from amino acid residues 351 to 541. The IL-1Rrp1 subunit protein encoded by SEQ ID NO:7 includes an extracellular domain of 322 amino acids (residues 1-322 of SEQ ID NO:8) that includes a signal peptide of 18 amino acids (residues 1-18 of SEQ ID NO:8); a transmembrane region of 25 amino acids (residues 323 to 347 of SEQ ID NO:8); and, a cytoplasmic domain from amino acid residues 348 to 537. Additionally, IL-1Rrp1 is described in U.S. Pat. No. 5,776,731 and AcPL is described in copending applications Ser. No. 60/078,835 and Ser. No. 60/072,301, incorporated herein by reference.

Preferably the polypeptide subunits of the dimeric IL-18 receptors are soluble fragments of IL-1Rrp1 and AcPL polypeptides which together form heteromer complexes having the desired activity. Such polypeptides include those lacking all or part of the transmembrane region and the cytoplasmic domain of the protein. Thus, for example, a heteromer receptor complex of the present invention can include at least one subunit that is the extracellular domain of SEQ ID NO:2 or SEQ ID NO:6 and at least one subunit that is the extracellular domain of SEQ ID NO:4 or SEQ ID NO:8. These soluble extracellular domains of AcPL and IL-1Rrp1 can include or exclude their signal peptide. Thus, in another embodiment, a heteromeric IL-18 receptor includes amino acid residues 1-356 or residues 15-356 of SEQ ID NO:2 or SEQ ID NO:6, and amino acid residues 1-329 or residues 20-329 of SEQ ID NO:4, or amino acid residues 1-325 or residues 19-322 of SEQ ID NO:8. The desirability of including the signal sequence depends on such factors as the position of the AcPL or IL-1Rrp1 in the fusion protein and the intended host cells when the receptor is to be produced via recombinant DNA technology. In preferred embodiments, a DNA construct encoding one of the soluble AcPL or soluble IL-1Rrp1 fragments is fused to a DNA construct encoding the constant region of an immunoglobulin heavy chain and a DNA construct encoding the other of the soluble AcPL or soluble IL-1Rrp1 fragment is fused to DNA encoding the constant region of an immunoglobulin light chain.

Alternatively, the IL-18 receptor may comprise IL-1Rrp1 or soluble IL-1Rrp1 fragments non-covalently complexed with AcPL or soluble AcPL fragments. Non-covalent bonding of IL-1Rrp1 to AcPL may be achieved by any suitable means that does not interfere with the receptor's ability to bind IL-18. In one approach, a first compound is attached to IL-1Rrp1 and a second compound that will non-covalently bond to the first compound is attached to AcPL. Examples of such compounds are biotin and avidin. The receptor is thus formed through the non-covalent interactions of biotin with avidin. In one embodiment of the invention, IL-1Rrp1 and AcPL are recombinant polypeptides, each purified from recombinant cells and then non-covalently bonded together to form the receptor. A host cell may be transformed with two different expression vectors such that both IL-1Rrp1 and AcPL are produced by the recombinant host cell. IL-1Rrp1 and AcPL produced by such transformed host cells may associate to form a complex through non-covalent interactions. When such transformed cells express the membrane-bound forms of the proteins, such cells are useful in various assays, including competition assays.

The binding assay described in example 1 compares the binding of IL-18 by supernatant from cells transfected with IL-1Rrp1 alone, AcPL alone and a combination of IL-1Rrp1 and AcPL. Supernatants from cells coexpressing IL-1Rrp1 and AcPL exhibited high levels of IL-18 binding; supernatants from cells expressing IL-1Rrp1 alone exhibited low levels of IL-18 binding; and, supernatant from cells transfected with AcPL alone do not bind IL-18. The NFκB induction assay described in example 2 demonstrates that cells transfected with IL-1Rrp1 alone and cells transfected with AcPL alone are not responsive to IL-18 stimulation. However, cells co-transfected with both IL-1Rrp1 and AcPL and stimulated with IL-18 greatly enhanced NFκB induction.

As used herein, the terms IL-1Rrp1 and AcPL include variants and truncated forms of the native proteins that possess the desired biological activity. Variants produced by adding, substituting, or deleting amino acid(s) in the native sequence are discussed in more detail below.

As described above, soluble IL-1Rrp1 and soluble AcPL polypeptides are preferred for certain applications. "Soluble IL-1Rrp1" as used in the context of the present invention refers to polypeptides that are substantially similar in amino acid sequence to all or part of the extracellular region of a native IL-1Rrp1 polypeptide and that, due to the lack of a transmembrane region that would cause retention of the polypeptide on a cell membrane, are secreted upon expression. Suitable soluble IL-1Rrp1 polypeptides retain the desired biological activity. Soluble IL-1Rrp1 may also include part of the transmembrane region or part of the cytoplasmic domain or other sequences, provided that the soluble IL-1Rrp1 protein is capable of being secreted.

Likewise, the term "soluble AcPL" as used herein refers to proteins that are substantially similar in amino acid sequence to all or part of the extracellular region of a native AcPL polypeptide and are secreted upon expression but retain the desired biological activity. Soluble AcPL may include part of the transmembrane region, cytoplasmic domain, or other sequences, as long as the polypeptide is secreted.

In one embodiment, soluble IL-1Rrp1 and AcPL polypeptides include the entire extracellular domain. To effect secretion, the soluble polypeptides comprise the native signal peptide or a heterologous signal peptide. Thus, examples of soluble IL-1Rrp1 polypeptides comprise amino acids 1-329 of SEQ ID NO:4 (human IL-1Rrp1) and amino acids 1-322 of SEQ ID NO:8 (murine IL-1Rrp1). Examples of soluble AcPL polypeptides comprise amino acids 1-356 of SEQ ID NO:2 (human AcPL) and amino acids 1-356 of SEQ ID NO:6 (murine AcPL).

A soluble fusion protein comprising the extracellular domain of IL-1Rrp1 of SEQ ID NO:4 fused to an antibody Fc region polypeptide and the extracellular domain of AcPL fused to an Fc region polypeptide, is described in example 1.

Soluble AcPL and soluble IL-1Rrp1 may be identified (and distinguished from their non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of AcPL or IL-1Rrp1 in the medium indicates that the protein was secreted from the cells and thus is a soluble form of the desired protein. Soluble AcPL and soluble IL-1Rrp1 may be naturally-occurring forms of these proteins. Alternatively, soluble fragments of AcPL and IL-1Rrp1 proteins may be produced by recombinant DNA technology or otherwise isolated, as described below.

The use of soluble forms of IL-1Rrp1 and AcPL is advantageous for certain applications. Purification of the proteins from recombinant host cells is facilitated, since the soluble proteins are secreted from the cells. Further, a receptor of the present invention comprising soluble IL-1Rrp1 and AcPL proteins is generally more suitable for intravenous administration.

With respect to the foregoing discussion of signal peptides and the various domains of the IL-1Rrp1 and AcPL proteins, the skilled artisan will recognize that the above-described boundaries of such regions of the proteins are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. Thus, soluble IL-1Rrp1 and AcPL polypeptides comprising the extracellular domain include those having a C-terminal amino acid that may vary from that identified above as the C-terminus of the extracellular domain. Further, post-translational processing that can vary according to the particular expression system employed may yield proteins having differing N-termini. Such variants that retain the desired biological activities are encompassed by the terms "IL-1Rrp1 polypeptides" and "AcPL polypeptides" as used herein.

Truncated IL-1Rrp1 and AcPL, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. Oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The well known polymerase chain reaction procedure also may be employed to isolate a DNA sequence encoding a desired protein fragment. Oligonucleotide primers comprising the desired termini of the fragment are employed in such a polymerase chain reaction. Any suitable PCR procedure may be employed. One such procedure is described in Saiki et al., *Science* 239:487 (1988). Another is described in *Recombinant DNA Methodology*, Wu et al., eds., Academic Press Inc., San Diego (1989), pp. 189-196. In general, PCR reactions involve combining the 5' and 3' oligonucleotide primers with template DNA (in this case, IL-1Rrp1 or AcPL DNA) and each of the four deoxynucleoside triphosphates, in a suitable buffered solution. The solution is heated, (e.g., from 95° C. to 100° C.) to denature the double-stranded DNA template and is then cooled before addition of a DNA polymerase enzyme. Multiple cycles of the reactions are carried out in order to amplify the desired DNA fragment.

The AcPL polypeptide is attached to the IL-1Rrp1 polypeptide through a covalent or non-covalent linkage. Covalent attachment is preferred for certain applications, e.g. in vivo use, in view of the enhanced stability generally conferred by covalent, as opposed to non-covalent, bonds. In constructing the receptor of the present invention, covalent linkage may be accomplished via cross-linking reagents, peptide linkers, or any other suitable technique.

Numerous reagents useful for cross-linking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains, thus linking one polypeptide to another.

One type of peptide linker that may be employed in the present invention separates AcPL and the IL-1Rrp1 domains by a distance sufficient to ensure that each domain properly folds into the secondary and tertiary structures necessary for the desired biological activity. The linker also should allow the extracellular domains of AcPL and IL-1Rrp1 to assume the proper spatial orientation to form the binding site for IL-18.

Suitable peptide linkers are known in the art, and may be employed according to conventional techniques. Among the suitable peptide linkers are those described in U.S. Pat. Nos. 4,751,180 and 4,935,233, which are hereby incorporated by reference. A peptide linker may be attached to by any of the conventional procedures used to attach one polypeptide to another. The cross-linking reagents available from Pierce Chemical Company as described above are among those that may be employed. Amino acids having side chains reactive with such reagents may be included in the peptide linker, e.g., at the termini thereof. Preferably, a fusion protein comprising AcPL joined to IL-1Rrp1 via a peptide linker is prepared by recombinant DNA technology.

In one embodiment of the invention, AcPL and IL-1Rrp1 are linked via polypeptides derived from immunoglobulins.

Preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). As one example, a polypeptide derived from the Fc region of an antibody may be attached to the C-terminus of IL-1Rrp1. A separate Fc polypeptide is attached to the C-terminus of AcPL. Disulfide bonds form between the two Fc polypeptides (e.g., in the so-called hinge region, where interchain disulfide bonds are normally present in antibody molecules), producing a heterodimer comprising the AcPL/Fc fusion protein linked to the IL-1Rrp1/Fc fusion protein. Advantageously, host cells are co-transfected with two different expression vectors, one encoding soluble IL-1Rrp1/Fc and the other encoding soluble AcPL/Fc. The heterodimer is believed to form intracellularly or during secretion.

The term "Fc polypeptide" as used herein includes native and mutein forms, as well as truncated Fc polypeptides containing the hinge region that promotes dimerization. cDNA encoding a single chain polypeptide derived from the Fc region of a human IgG1 antibody can be cloned into the pBluescript SK® cloning vector (Stratagene Cloning Systems, LaJolla, Calif.) to produce a recombinant vector designated hIgG1Fc. A unique BglII site is positioned near the 5' end of the inserted Fc encoding sequence. An SpeI site is immediately downstream of the stop codon. The Fc polypeptide encoded by the cDNA extends from the N-terminal hinge region to the native C-terminus, i.e., is an essentially full-length antibody Fc region. One suitable mutein of this Fc polypeptide is described in U.S. patent application Ser. No. 08/097,827, hereby incorporated by reference. The mutein exhibits reduced affinity for Fc receptors.

Homodimers comprising two IL-1Rrp1/Fc polypeptides or two AcPL/Fc polypeptides linked via disulfide bonds are also produced by certain of the transfected host cells disclosed herein. The homodimers may be separated from each other and from the heterodimer by virtue of differences in size (e.g., by gel electrophoresis). The heterodimer also may be purified by sequential immunoaffinity chromatography (described below).

Il-18 receptor complexes of the present invention include fusion proteins of the constant region of an antibody light chain (or fragment thereof) and the constant region of an antibody heavy chain (or a fragment thereof). The constant region of the heavy chain can include all four of its constant region domains or portion of the domains, including the $C_H1$ which associates with the light chain, the H hinge region, and the $CH_2$ and $CH_3$ domains which are responsible for the dimerization of the heavy chain molecules. Within the scope of the foregoing fusion proteins are tetramers that are formed by two dimers which link heavy chain/light chain dimers via disulfide linkages between their respective heavy chain regions.

With respect to immunoglobulin light chain polypeptides, polypeptides of the κ family and the λ family are suitable in the practice of this invention. Thus, any type of immunoglobulin dimers or tetramer including IgM, IgD, IgG, IgA and IgE can be the basis of the heteromer molecules of the present invention.

In accordance with the present invention, functional heteromeric polypeptides can be prepared by the association between multiple heavy and multiple light chain molecules which normally associate with one another. For example, the constant region of human IgG1 will associate with the constant region of human light chain kappa (designated $C_{kappa}$). The amino acid sequence of hIgG1 constant region has been reported (Ellison, J W, Berson, B J and Hood, L E 1982). The nucleotide sequence of a human immunoglobulin C gamma 1 gene is reported. (Nuc. Acids Res. 10: 4071 and Walls, M A, Hsiao, K C and Harris, L J 1993). Vectors for the expression of PCR-amplified immunoglobulin variable domains with human constant regions are disclosed. (Nuc. Acids Res. 21:2921) The sequence of human light chain $C_{kappa}$ has also been reported (Shuford, W, Raff, H V, Finley, J W, Esselstyn, J and Harris, L J. 1991) Effect of light chain V-region duplication on IgG oligomerization and in vivo efficacy. Science 252:724 and Steinberger, P, Kraft, D and Valenta, R (1996). Construction of a combinatorial IgE library from an allergic patient. Isolation and characterization of human IgE Fabs with specificity for the major timothy grass pollen allergen, Ph1 p 5. J. Biol. Chem., 271:10972).

IL-18 receptor embodiments that include heavy and light chain antibody regions are fusion proteins represented by the formulae:

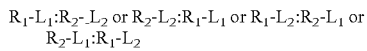

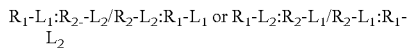

in which $L_1$ is an immunoglobulin heavy chain fragment, the N terminus of which extends at least through the $C_H1$ region; $L_2$ is an immunoglobulin light chain fragment; $R_1$ is AcPL or an AcPL fragment; $R_2$ is IL-1Rrp1 or an IL-1Rrp1 fragment;: designates linkages between a heavy chain and light chain antibody region, and/designates linkages between a heavy chain and a heavy chain antibody region. In the case of a dimer, the resulting fusion polypeptide includes two receptor subunits joined by a heavy chain/light chain. In the case of the tetramer, the fusion protein includes four receptor subunits and resembles an antibody in structure, displaying the IL-18 binding site bivalently.

To obtain the foregoing fusion polypeptides, cDNA encoding an antibody heavy chain polypeptide derived from human IgG1 antibody ($CH_1$—H—$CH_2$—$CH_3$) can be cloned into the pDC409 expression vector to produce a recombinant vector designated hIgG1. A unique BglII site is positioned near the 5' end of the inserted heavy chain encoding sequence. A NotI site is immediately downstream of the stop codon. The heavy chain polypeptide, encoded by the cDNA extends from the N-terminus of the $CH_1$ region to the native C-terminus. To obtain an antibody light chain cDNA encoding a single chain polypeptide derived from the human kappa chain constant regions can be cloned in the pDC409 expression vector to produce a recombinant vector designated hIgκ. This sequence is flanked at the 5' end by a unique BglII site and at the 3' end by a unique NotI site. Embodiments of the present invention that incorporate such antibody polypeptides include a first fusion polypeptide comprising AcPL (or a fragment thereof) upstream of the constant region of an antibody light chain (or a fragment thereof) and a second fusion polypeptide comprising IL-1Rrp1 upstream of the constant region of an antibody heavy chain (or a heavy chain fragment), the N-terminus of which extends at least through the $C_H1$ region. Disulfide bond(s) form between the AcPL light chain fusion polypeptide and the IL-1Rrp1-heavy chain fusion polypeptide, thus producing a receptor of the present invention. As a further alternative, an IL-1Rrp1-antibody light chain fusion polypeptide is prepared and combined with (disulfide bonded to) a fusion polypeptide comprising AcPL-antibody heavy chain fusion polypeptide. When two of the foregoing disulfide bonded molecules are combined, additional disulfide bonds form between the two antibody regions.

The resulting receptor of the present invention comprising four fusion polypeptides resembles an antibody in structure and displays the IL-18 binding site bivalently.

The AcPL and IL-1Rrp1 polypeptides may be separately purified from cellular sources, and then linked together. Alternatively, the receptor of the present invention may be produced using recombinant DNA technology. The AcPL and IL-1Rrp1 polypeptides may be produced separately and purified from transformed host cells for subsequent covalent linkage. In one embodiment of the present invention, a host cell is transformed/transfected with foreign DNA that encodes AcPL and IL-1Rrp1 as separate polypeptides. The two polypeptides may be encoded by the same expression vector with start and stop codons for each of the two genes, or the recombinant cells may be co-transfected with two separate expression vectors. In another embodiment, the receptor is produced as a fusion protein in recombinant cells.

In one embodiment of the present invention, the receptor protein is a recombinant fusion protein of the formula:

$$R_1\text{-}L\text{-}R_2 \text{ or } R_2\text{-}L\text{-}R_1$$

wherein $R_1$ represents AcPL or an AcPL fragment; $R_2$ represents IL-1Rrp1 or an IL-1Rrp1 fragment; and L represents a peptide linker.

The fusion proteins of the present invention include constructs in which the C-terminal portion of AcPL is fused to the linker which is fused to the N-terminal portion of IL-1Rrp1, and also constructs in which the C-terminal portion of IL-1Rrp1 is fused to the linker which is fused to the N-terminal portion of AcPL. AcPL is covalently linked to IL-1Rrp1 in such a manner as to produce a single protein which retains the desired biological activities of AcPL and IL-1Rrp1. The components of the fusion protein are listed in their order of occurrence (i.e., the N-terminal polypeptide is listed first, followed by the linker and then the C-terminal polypeptide).

A DNA sequence encoding a fusion protein is constructed using recombinant DNA techniques to insert separate DNA fragments encoding AcPL and IL-1Rrp1 into an appropriate expression vector. The 3' end of a DNA fragment encoding AcPL is ligated (via the linker) to the 5' end of the DNA fragment encoding IL-1Rrp1 with the reading frames of the sequences in phase to permit translation of the mRNA into a single biologically active fusion protein. Alternatively, the 3' end of a DNA fragment encoding IL-1Rrp1 may be ligated (via the linker) to the 5' end of the DNA fragment encoding AcPL, with the reading frames of the sequences in phase to permit translation of the mRNA into a single biologically active fusion protein. A DNA sequence encoding an N-terminal signal sequence may be retained on the DNA sequence encoding the N-terminal polypeptide, while stop codons, which would prevent read-through to the second (C-terminal) DNA sequence, are eliminated. Conversely, a stop codon required to end translation is retained on the second DNA sequence. DNA encoding a signal sequence is preferably removed from the DNA sequence encoding the C-terminal polypeptide.

A DNA sequence encoding a desired polypeptide linker may be inserted between, and in the same reading frame as, the DNA sequences encoding AcPL and IL-1Rrp1 using any suitable conventional technique. For example, a chemically synthesized oligonucleotide encoding the linker and containing appropriate restriction endonuclease cleavage sites may be ligated between the sequences encoding AcPL and IL-1Rrp1.

Alternatively, a chemically synthesized DNA sequence may contain a sequence complementary to the 3' terminus (without the stop codon) of either AcPL and IL-1Rrp1, followed by a linker-encoding sequence which is followed by a sequence complementary to the 5' terminus of the other of AcPL and IL-1Rrp1. Oligonucleotide directed mutagenesis is then employed to insert the linker-encoding sequence into a vector containing a direct fusion of AcPL and IL-1Rrp1.

The present invention provides isolated DNA sequences encoding the above-described fusion proteins comprising AcPL, IL-1Rrp1, and a peptide linker. DNA encoding AcPL polypeptides disclosed herein is also provided, as is DNA encoding AcPL polypeptides fused to immunoglobulin-derived polypeptides. AcPL-encoding DNA encompassed by the present invention includes, for example, cDNA, chemically synthesized DNA, DNA isolated by PCR, genomic DNA, and combinations thereof.

Also provided herein are recombinant expression vectors containing the isolated DNA sequences. "Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein which is transcribed into mRNA and translated into protein, and (3) appropriate transcription and translation initiation and termination sequences. The choice of promoter and other regulatory elements generally varies according to the intended host cell.

In the expression vectors, regulatory elements controlling transcription or translation are generally derived from mammalian, microbial, viral or insect genes. The ability to replicate in a host, usually conferred by an origin of replication, and a selection gene to facilitate recognition of transformants may additionally be incorporated. Vectors derived from retroviruses also may be employed.

DNA regions are operably linked when they are functionally related to each other. For example, DNA encoding a signal peptide (secretory leader) is operably linked to DNA for a polypeptide if the polypeptide is expressed as a precursor that is secreted through the host cell membrane; a promoter is operably linked to a coding sequence if it controls the transcription of the sequence; and a ribosome binding site is operably linked to a coding sequence if it is positioned so as to permit translation. Generally, "operably linked" means contiguous and, in the case of secretory leaders, contiguous and in reading frame.

Transformed host cells are cells which have been transformed or transfected with foreign DNA using recombinant DNA techniques. In the context of the present invention, the foreign DNA includes a sequence encoding the inventive proteins. Host cells may be transformed for purposes of cloning or amplifying the foreign DNA, or may be transformed with an expression vector for production of the protein. Suitable host cells include prokaryotes, yeast or higher eukaryotic cells. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotes include gram negative or gram positive organisms, for example *E. coli* or bacilli. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli, Bacillus* subtilis, Salmonella typhimurium, and various species within the genera *Pseudomonas, Streptomyces*, and *Staphylococcus*, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and this provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermoinducible repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

The recombinant receptor protein may also be expressed in yeast hosts, preferably from *Saccharomyces* species, such as *S. cerevisiae*. Yeast of other genera such as *Pichia* or *Kluyveromyces* may also be employed. Yeast vectors will generally contain an origin of replication from the 2 µm yeast plasmid or an autonomously replicating sequence (ARS), a promoter, DNA encoding the receptor fusion protein, sequences for polyadenylation and transcription termination and a selection gene. Preferably, yeast vectors will include an origin of replication and selectable markers permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* ($Amp^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al., (*Nature* 300:724, 1982). The yeast α-factor leader, which directs secretion of heterologous proteins, can be inserted between the promoter and the structural gene to be expressed. See, e.g., Kurjan et al., *Cell* 30:922, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al., *Proc. Natl. Acad. Sci. USA* 75:1929, (1978), selecting for Trp$^+$ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include L cells, C127, 3T3, Chinese hamster ovary (CHO), HeLa, and BHK cell lines. Additional suitable mammalian host cells include CV-1 cells (ATCC CCL70) and COS-7 cells (ATCC CRL 1651; described by Gluzman, *Cell* 23:175, 1981), both derived from monkey kidney. Another monkey kidney cell line, CV-1/EBNA (ATCC CRL 10478), was derived by transfection of the CV-1 cell line with a gene encoding Epstein-Barr virus nuclear antigen-1 (EBNA-1) and with a vector containing CMV regulatory sequences (McMahan et al., *EMBO J.* 10:2821, 1991). The EBNA-1 gene allows for episomal replication of expression vectors, such as HAV-EO or pDC406, that contain the EBV origin of replication.

Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers et al., *Nature* 273:113, 1978). Smaller or larger SV40 fragments may also be used, provided the approximately 250 bp sequence extending from the Hind III site toward the BglI site located in the viral origin of replication is included.

Exemplary vectors can be constructed as disclosed by Okayama and Berg (*Mol. Cell. Biol.* 3:280, 1983). One useful system for stable high level expression of mammalian receptor cDNAs in C127 murine mammary epithelial cells can be constructed substantially as described by Cosman et al. (*Mol. Immunol.* 23:935, 1986). Vectors derived from retroviruses also may be employed.

When secretion of the AcPL and/or IL-1Rrp1 protein from the host cell is desired, the expression vector may comprise DNA encoding a signal or leader peptide. In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

The present invention provides a process for preparing the recombinant proteins of the present invention, comprising culturing a host cell transformed with an expression vector comprising a DNA sequence that encodes said protein under conditions that promote expression. The desired protein is then purified from culture media or cell extracts. The desired protein may be AcPL, IL-1Rrp1 or the heterodimeric receptor, for example. Cell-free translation systems could also be employed to produce the desired protein using RNA derived from the novel DNA of the present invention.

As one example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise IL-18. An IL-18 affinity matrix may be prepared by coupling recombinant human IL-18 to cyanogen bromide-activated Sepharose (Pharmacia) or Hydrazide Affigel (Biorad), according to manufacturer's recommendations. Sequential immunopurification using antibodies bound to a suitable support is preferred. Proteins binding to an antibody specific for AcPL are recovered and contacted with antibody specific for IL-1Rrp1 on an insoluble support. Proteins immunoreactive with both antibodies may thus be identified and isolated.

Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify a fusion protein.

Some or all of the foregoing purification steps, in various combinations, can be employed to provide an essentially homogeneous recombinant protein. Recombinant cell culture enables the production of the fusion protein free of those contaminating proteins which may be normally associated with IL-1Rrp1 or AcPL as they are found in nature in their respective species of origin, e.g., on the surface of certain cell types.

The foregoing purification procedures are among those that may be employed to purify non-recombinant receptors of the present invention as well. When linking procedures that may produce homodimers (IL-1Rrp1-linker-IL-1Rrp1 and AcPL-linker-AcPL) are employed, purification procedures that separate the heterodimer from such homodimers are employed. An example of such a procedure is sequential immunopurification as discussed above. In one embodiment, AcPL (recombinant or non-recombinant) is purified such that no bands corresponding to other (contaminating) proteins are detectable by SDS-PAGE.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984), involving two sequential, reversed-phase HPLC steps for purification of a recombinant protein on a preparative HPLC column.

The DNA or amino acid sequences of IL-1Rrp1 or AcPL may vary from those presented in SEQ ID NO:1, SEQ ID NO:3, SEQ ID NO:5 and SEQ ID NO:7. Due to the known degeneracy of the genetic code, there can be considerable variation in nucleotide sequences encoding the same amino acid sequence. In addition, DNA sequences capable of hybridizing to the native DNA sequence of SEQ ID NO:1, SEQ ID NO:3, SEQ ID NO:5 or SEQ ID NO:7 under moderately stringent or highly stringent conditions, and which encode a biologically active IL-1Rrp1 or AcPL polypeptide, are also considered to be IL-1Rrp1-encoding or AcPL-encoding DNA sequences, in the context of the present invention. Such hybridizing sequences include but are not limited to variant sequences such as those described below, and DNA derived from other mammalian species.

Moderately stringent conditions include conditions described in, for example, Sambrook et al, *Molecular Cloning: A Laboratory Manual*, 2nd ed., Vol. 1, pp 1.101-104, Cold Spring Harbor Laboratory Press, 1989. Conditions of moderate stringency, as defined by Sambrook et al., include use of a prewashing solution of 5×SSC, 0.5% SDS, 1.0 mM EDTA (pH 8.0) and hybridization conditions of about 55° C., 5×SSC, overnight. Highly stringent conditions include higher temperatures of hybridization and washing. The skilled artisan will recognize that the temperature and wash solution salt concentration may be adjusted as necessary according to factors such as the length of the probe, wherein said conditions include hybridization at 68° C. followed by washing in 0.1×SSC/0.1% SDS at 63-68° C. In another embodiment, the present invention provides a heterodimeric receptor comprising AcPL and IL-1Rrp1, wherein the AcPL and the IL-1Rrp1 are encoded by DNA that hybridizes to the DNA of SEQ ID NO:1 or SEQ ID NO:5, or SEQ ID NO:3 or SEQ ID NO:7, respectively, under moderately or highly stringent conditions.

Further, certain mutations in a nucleotide sequence which encodes AcPL or IL-1Rrp1 will not be expressed in the final protein product. For example, nucleotide substitutions may be made to enhance expression, primarily to avoid secondary structure loops in the transcribed mRNA (see EP 75,444A). Other alterations of the nucleotide sequence may be made to provide codons that are more readily translated by the selected host, e.g., the well-known *E. coli* preference codons for *E. coli* expression.

The amino acid sequence of native IL-1Rrp1 or AcPL may be varied by substituting, deleting, adding, or inserting one or more amino acids to produce a IL-1Rrp1 or AcPL variant. Variants that possess the desired biological activity of the native IL-1Rrp1 and AcPL proteins may be employed in the receptor of the present invention. Assays by which the biological activity of variant proteins may be analyzed are described in the examples below. Biologically active IL-1Rrp1 polypeptides are capable of binding IL-18. The desired biological activity of the AcPL polypeptides disclosed herein is the ability to enhance the binding of IL-18 when AcPL is joined to IL-1Rrp1, compared to the level of IL-18 binding to IL-1Rrp1 alone.

Alterations to the native amino acid sequence may be accomplished by any of a number of known techniques. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craig (*BioTechniques*, Jan. 1985, 12-19); Smith et al. (*Genetic Engineering: Principles and Methods*, Plenum Press, 1981); U.S. Pat. Nos. 4,518,584, and 4,737,462, which are incorporated by reference herein.

Bioequivalent variants of AcPL and IL-1Rrp1 may be constructed by, for example, making various substitutions of amino acid residues or deleting terminal or internal amino acids not needed for biological activity. In one embodiment of the invention, the variant amino acid sequence is at least 80% identical, preferably at least 90% identical, to the native sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math. 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Generally, substitutions should be made conservatively; i.e., the most preferred substitute amino acids are those having physiochemical characteristics resembling those of the residue to be replaced. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Cysteine residues can be deleted or replaced with other amino acids to prevent formation of unnecessary or incorrect intramolecular disulfide bridges upon renaturation. Hydrophilic amino acids may be substituted for hydrophobic amino acids in the transmembrane region and/or intracellular domain of IL-1Rrp1 and AcPL to enhance water solubility of the proteins.

Adjacent dibasic amino acid residues may be modified to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. These amino acid pairs, which constitute KEX2 proteases processing sites, are found at residues 98-99, 323-333, 333-334, 472-473 and 475-476 of the AcPL protein of SEQ ID NO:2. These KEX2 sites are found at positions 113-114, 314-315, 364-365, 437-438, and 465-466 of the IL-1Rrp1 protein of SEQ ID NO:4. Lys-Lys pairings are considerably less susceptible to KEX2 cleavage, and conversion of Arg-Lys or Lys-Arg to Lys-Lys represents a conservative and preferred approach to inactivating KEX2 sites.

The present invention also includes proteins with or without associated native-pattern glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where A1 is any amino acid except Pro, and Z is Ser or Thr. In this sequence, asparagine provides a side chain amino group for covalent attachment of carbohydrate.

The AcPL amino acid sequence in SEQ ID NO:2 contains 4 such N-glycosylation sites, all found in the extracellular domain, at amino acids 21-23, 119-121, 152-254 and 345-347. The extracellular domain of IL-1Rrp1 comprises N-glycosylation sites at positions 91-93, 102-104, 150-153, 168-170, 197-199, 203-205, 236-238, and 297-299 of SEQ ID NO:4. Such a site can be eliminated by substituting another amino acid for Asn or for residue Z, deleting Asn or Z, or inserting a non-Z amino acid between $A_1$ and Z, or an amino acid other than Asn between Asn and $A_1$. Known procedures for inactivating N-glycosylation sites in proteins include those described in U.S. Pat. No. 5,071,972 and EP 276,846.

Variants of the receptor proteins of the present invention also include various structural forms of the primary protein which retain biological activity. Due to the presence of ionizable amino and carboxyl groups, for example, a receptor protein may be in the form of acidic or basic salts, or may be in neutral form. Individual amino acid residues may also be modified by oxidation or reduction.

The primary amino acid structure also may be modified by forming covalent or aggregative conjugates with other chemical moieties, such as glycosyl groups, lipids, phosphate, acetyl groups and the like. Covalent derivatives are prepared by linking particular functional groups to amino acid side chains or at the N- or C-termini. Other derivatives of the receptor protein within the scope of this invention include covalent or aggregative conjugates of the receptor protein with other proteins or polypeptides, such as by synthesis in recombinant culture as N- or C-terminal fusions. For example, the conjugated polypeptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Peptides may be fused to the desired protein (e.g., via recombinant DNA techniques) to facilitate purification or identification. Examples include poly-His or the Flag® peptide (Hopp et al., *Bio/Technology* 6:1204, 1988, and U.S. Pat. No. 5,011,912). The Flag® peptide is highly antigenic and provides an epitope reversibly bound by a specific monoclonal antibody, enabling rapid assay and facile purification of expressed recombinant protein. Expression systems useful for fusing the Flag® octapeptide to the N- or C-terminus of a given protein are available from Eastman Kodak Co., Scientific Imaging Systems Division, New Haven, Conn., as are monoclonal antibodies that bind the octapeptide.

Dimer IL-18 receptor complexes that include naturally occurring variants of IL-1Rrp1 and AcPL are also encompassed by the present invention. Examples of such variants are proteins that result from alternative mRNA splicing events or from proteolytic cleavage of the AcPL and IL-1Rrp1 protein, wherein the desired biological activity is retained. Alternative splicing of mRNA may yield a truncated but biologically active AcPL and IL-1Rrp1 protein, such as a naturally occurring soluble form of the protein. Variations attributable to proteolysis include, for example, differences in the N-or C-termini upon expression in different types of host cells, due to proteolytic removal of one or more terminal amino acids from the AcPL or IL-1Rrp1 protein (generally from 1-5 terminal amino acids).

The present invention also provides a pharmaceutical composition comprising a receptor protein of the present invention with a physiologically acceptable carrier or diluent. Such carriers and diluents will be nontoxic to recipients at the dosages and concentrations employed. Such compositions may, for example, comprise the receptor protein in a buffered solution, to which may be added antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients. The receptor of the present invention may be administered by any suitable method in a manner appropriate to the indication, such as intravenous injection, local administration, continuous infusion, sustained release from implants, etc.

Heterodimeric receptors of the present invention are useful as an IL-18 binding reagent. This receptor, which preferably comprises soluble AcPL and soluble IL-1Rrp1, has applications both in vitro and in vivo. The receptors may be employed in in vitro assays, e.g., in studies of the mechanism of transduction of the biological signal that is initiated by binding of IL-18 to this receptor on a cell. Such receptors also could be used to inhibit a biological activity of IL-18 in various in vitro assays or in vivo procedures. In one embodiment of the invention, the inventive receptor is administered to bind IL-18, thus inhibiting binding of the IL-18 to endogenous cell surface receptors. Biological activity mediated by such binding of IL18 to the cells thus is also inhibited.

IL-1Rrp1 alone binds IL-18, but with relatively low affinity (Torigoe et al. *J. Biol. Chem* 272:2573, 1997). Receptors of the present invention, produced by cells co-transfected with AcPL and IL-1Rrp1-encoding DNA, for example, bind IL-18 with high affinity. Such receptors of the present invention may be employed when inhibition of an IL-18-mediated activity is desired. In addition, use of the receptors of the present invention in vitro assays offers the advantage of allowing one to determine that the assay results are attributable to binding of IL18.

In one embodiment of the invention, a heterodimeric receptor comprising AcPL and IL-1Rrp1 is administered in vivo to inhibit a biological activity of IL-18. IL-18 is known to mediate NFκB activity and acts as a stimulator of Th1 cell growth and differentiation, and is a potent inducer of γ-interferon production from Th1 cells. IL-18 also enhances NK cell killing activity and has been implicated in septic shock, liver destruction, and diabetes. When these or other biological effects of IL-18 are undesirable, a receptor of the present invention may be administered to bind IL-18 and ameliorate the effects of IL-18 activity.

The inventive receptor may be administered to a patient in a therapeutically effective amount to treat a disorder mediated by IL-18. A disorder is said to be mediated by IL-18 when IL-18 causes (directly or indirectly) or exacerbates the disorder. Soluble receptor proteins can be used to competitively bind to IL-18, thereby inhibiting binding of IL-18 to endogenous cell surface receptors.

Heterodimeric receptors comprising AcPL linked to IL-1Rrp1 also find use in assays for biological activity of IL-18 proteins, which biological activity is measured in terms of binding affinity for the receptor. To illustrate, the receptor may be employed in a binding assay to measure the biological activity of an IL-18 fragment, variant, or mutein. The receptor is useful for determining whether biological activity of IL-18 is retained after modification of an IL-18 protein (e.g., chemical modification, mutation, etc.). The binding affinity of the modified IL-18 protein for the receptor is compared to that of an unmodified IL18 protein to detect any adverse impact of the modification on biological activity. Biological activity thus can be assessed before the modified protein is used in a research study or assay, for example.

The heterodimeric receptors also find use as reagents that may be employed by those conducting "quality assurance" studies, e.g., to monitor shelf life and stability of IL-18 proteins under different conditions. The receptors may be used to confirm biological activity (in terms of binding affinity for the receptor) in IL-18 proteins that have been stored at different temperatures, for different periods of time, or which have been produced in different types of recombinant expression systems, for example.

The following examples are provided to illustrate certain embodiments of the invention, and are not to be construed as limiting the scope of the invention.

EXAMPLES

Example 1

In Vitro Precipitation Experiments

In order to determine whether AcPL, IL-1Rrp1 or combinations of the two polypeptides bind IL-18, several Fc fusion proteins were prepared and tested as follows. An expression vector encoding a soluble AcPL/Fc fusion protein, which comprised a truncated extracellular domain of AcPL fused to the N-terminus of an Fc region polypeptide derived from an antibody, was constructed as follows. A recombinant expression vector comprising AcPL DNA in vector pDC304, was PCR amplified utilizing primers containing the desired in-frame restriction sites on the 5' and 3' ends. The resulting fragment, which includes the 5' end of the AcPL DNA, terminating at nucleotide 1551 of SEQ ID NO:1, with introduced SalI and BglII sites at the 5' and 3' ends, respectively, was isolated, by conventional techniques.

A recombinant vector designated pDC412-hIgG1Fc comprises the Fc polypeptide-encoding cDNA (—H—$CH_2$—$CH_3$ only). Vector pDC412-hIgG1Fc was digested with the restriction enzymes SalI and BglII, which cleave in the polylinker region of the vector, upstream of the Fc polypeptide-encoding cDNA.

The AcPL-encoding DNA fragment isolated above was ligated into a SalI/BglII-digested pDC412-hIgG1Fc such that the Fc polypeptide DNA was fused to the 3' end of the AcPL DNA. The resulting expression vector encoded a fusion protein comprising amino acids 1-356 of the AcPL sequence of SEQ ID NO:2, followed by the H—$CH_2$—$CH_3$ region of hIgG1Fc.

An expression vector encoding a soluble human IL-1Rrp1/Fc fusion protein was constructed as follows. A recombinant vector that includes IL-1Rrp1 cDNA was PCR amplified with gene-specific primers containing the desired restriction sites. The resulting fragment, which includes the 5' end of IL-1Rrp1 was isolated by conventional techniques. This IL-1Rrp1 fragment, digested with Asp718 and BglII, was combined with the hIgG1Fc fragment described above and digested with BglII and NotI. The resulting digest fragments were ligated to pDC304 digested with Asp718 and Not I. The resulting IL-1Rrp1/Fc fusion protein encoded by the recombinant vector comprises (from N- to C-terminus) amino acids 1-329 of SEQ ID NO:4, followed by the H—$CH_2$—$CH_3$ region of hIgG1/Fc.

In one sample set, COS-7 cells were transfected with a pDC206 control or pDC206-IL-18 vector. In another sample set of transfected COS-7 cells, the Fc fusion vectors described above were transfected. The total sample set was as follows:

| Sample | Cells transfected with vector(s) encoding: |
|---|---|
| A | empty pDC206 expression vector (control) |
| B | pDC206hIL-18 |
| 1 | pDC409 (control) |
| 2 | IL-1Rrp1/Fc |
| 3 | AcPL/Fc |
| 4 | AcPL/Fc and IL-1Rrp1/Fc |

Two days post transfection, samples A and B were starved 1 hour in cys/met-free medium, then labeled with [$^{35}$S-cys] [$^{35}$S-met]-containing medium for 6 hours. Supernatants were removed, subjected to centrifugation, and adjusted to 0.4M NaCl/1.0% Triton X-100 in the presence of protease inhibitors. The supernatants from cells transfected with the Fc fusion proteins of Samples 1-4 were removed at 2 days post transfection and centrifuged. Each Fc fusion supernatant was combined with either a) vector-transfected: or, b) IL-18 transfected $^{35}$S-labeled supernatants. Purified IL-1Rrp1/Fc-receptor protein was added to another portion of the radiolabeled supernatant as a control. Protein G-Sepharose was added to each experimental sample and precipitations were carried out overnight at 4° C. Then the samples were washed extensively in a 0.4M NaCl, 0.05% SDS, 1.0% NP-40 buffer and separated by electrophoresis in a 4-20% Tris-Glycine gel. The gel was fixed, amplified, dried and exposed to film. In order to assess total levels of protein and take into account unlabeled Fc-fusion proteins, a portion of each precipitate was analyzed on a separate 4-20% Tris-Glycine gel and silver stained.

Supernatants from cell samples 1-4 did not noticeably precipitate any proteins in the 10-30 Kd range from the control supernatant (Sample A). IL-18 (Sample B) was precipitated by supernatant from cell sample 2 (IL-1Rrp1Fc) but not by supernatant from cell sample 1 (control) or cell sample 3 (AcPL/Fc). Significantly more IL-18 was precipitated by supernatant from all sample 4 that was obtained from the cotransfection of IL-1Rrp1/Fc and AcPL/Fc.

Thus, IL-1Rrp1 is able to bind IL-18; AcPL is not able to bind IL-18; and, coexpressed IL-1Rrp1 and AcPL are able to bind Il-18 and the coexpressed proteins exhibit higher levels of binding of IL-18 than IL-1Rrp1alone. The silver stained gel shows that there is no more IL-1Rrp1 in supernatants transfected with Il-1Rrp1 and AcPL as compared to supernatants transfected with IL-1Rrp1 alone. This rules out the possibility that there is more IL-1Rrp1 expressed in these samples. The results indicate that the IL-18 binding affinity of an IL-1Rrp1 /AcPL dimer is greater than the affinity of IL-1Rrp1 alone.

Example 2

Induction of NFκB Activity

In order to determine the roles of IL-1Rrp1 and AcPL in IL-18 signaling, AcPL, IL-1Rrp1, and a combination of IL-1Rrp1 and AcPL were overexpressed in COS cells and S49.1 cells and the effect of IL-18 stimulation on NFκB activation was assessed.

COS-7 cells were transfected by the DEAE/Dextran method in a 12-well format. Each well was transfected with a total of 200 ng of the appropriate expression vector(s) and 800 ng of a NFκB-Luc reporter plasmid, which contains 3 NFκB sites mediating luciferase expression. Approximately $10^7$ S49.1 cells were transfected by electroporation in 0.7 mL with 40 μg of the NFκB-Luc reporter plasmid, and a total of 20 μg of the appropriate expression vector(s). Electroporations were performed at 960 μF and 320V.

The cells were incubated for 2 days, and then stimulated with 40 ng/mL of IL-18 (purchased from PeproTech) for 4 hours. Cells were washed, lysed, and assayed for luciferase activity using Luciferase Assay Reagents (purchased from Promega Corp.) according to the manufacturer's instructions.

COS7 or S49.1 cells that were transfected with control vector alone, vector encoding mIL-1Rrp1 alone, or vector encoding mAcPL alone were not responsive to mIL-18 stimulation. Furthermore, S49.1 cells transfected with mAcPL were not responsive to mIL-18 signaling when the transfection was in combination with an expression vector encoding mIL-1R type I or mIL-1RAcP. However, cells cotransfected with mAcPL and mIL-1Rrp1 and stimulated with mIL-18 showed an increase in NFκB DNA binding activity that was 10 fold in COS cells and 300 fold in S49.1 cells. COS7 cells transfected with hIL-1Rrp1 displayed no response to hIL-18 stimulation, while COS7 cells transfected with hAcPL alone and stimulated with hIL-18 showed an 8 fold increase in NFκB activity. This is attributed to the association of hAcPL with monkey IL-1Rrp1 endogenous to COS7 cells. Overexpression of hIL-1Rrp1 with hAcPL did not augment the stimulation of NFκB activity in response to hIL-18 over that seen in cells overexpressing hAcPL alone. This dramatic enhancement of NFκB activity indicates that AcPL and IL-1Rrp1 are subunits of the IL-18 receptor and cooperate to induce NFκB signaling in response to EL-18 stimulation.

Example 3

Preparing AcPL and IL-1Rrp1 Antibody Heavy and Light Chain Fusion Proteins

The following describes preparing fusion proteins that include AcPL and IL-1Rrp1 fused to an antibody heavy chain and antibody light chain polypeptide.

First, an expression vector encoding the entire constant region of human IgG1 with a linker region upstream is constructed. Such an expression vector facilitates the creation of fusion protein-encoding plasmids. PCR techniques are utilized to amplify the above mentioned IgG1 constant region with primers containing an upstream BglII site and a downstream NotI site. The resulting PCR generated fragment is digested, purified, and ligated to pDC412 which is digested with BglII and NotI. The pDC412-hIgG1 expression vector is then digested with SalI and BglII.

Next an expression vector containing the Ig κ constant domain preceded by a linker region and followed by a linker region and poly-His domain is prepared. The poly-His domain advantageously aids in the protein purification process. PCR techniques are utilized to amplify the constant region with primers containing a BglII-NotI fragment. The resulting PCR generated fragment is digested, purified, and ligated to pDC412. Soluble receptors of interest can be cloned upstream by utilizing the unique SalI and BglII sites.

To prepare an IL-1Rrp1-Cκ expression vector, the extracellular domain of IL-1Rrp1 is PCR amplified using primers containing SalI (5') and BglII (3') restriction sites. This purified and digested PCR product is ligated to SalI/BglII digested the pDC412-Ig κ expression vector to create an in-frame construct that encodes a fusion protein linking the soluble portion of IL-1Rrp1 to the constant region of Cκ.

To prepare an IL-1Rrp1-hIgG1 expression vector the SalI/BglII restriction fragment encoding soluble IL-1Rrp1 is removed from IL-1Rrp1-Cκ and ligated to pDC412-hIgG1 which has been digested with the same restriction enzymes. Since both vectors contain the BglII site in the same reading frame, this will readily generate a fusion between soluble IL-1Rrp1 and hIgG1.

To prepare an AcPL-Cκ expression vector, the extracellular domain of AcPL is PCR amplified using primers containing SalI (5') and BglII (3') restriction sites. This purified and digested PCR product then is ligated to SalI/BglII digested pDC412-Cκ to create an in-frame fusion protein linking the soluble portion of AcPL to the constant region of Cκ.

To prepare an AcPL-hIgG1 expression vector the SalI/BglII restriction fragment encoding soluble AcPL is removed from AcPL-cκ and ligated to pDC412-hIgG1 which has been digested with the same restriction enzymes. Since both vectors contain the BglII site in the same reading frame, this will readily generate a fusion between soluble AcPL and hIgG1.

COS-7 cells are transfected with the above described fusion vectors. The cells are cultured and the fusion proteins are collected as described in Example 1.

Example 4

Inhibition of an IL18 Induced NFκB Activity

Cos7 cells were transiently transfected in 12-well plates with 10 ng each of mIL-1Rrp1 and mAcPL expression vectors, and 50 ng of a 3×NFκB-Luciferase reporter plasmid per well. Two days post-transfection, cells were stimulated with 10 ng/ml mIL-18 (purchased from Peprotech) in the presence of increasing amounts of various receptor-Fc fusion proteins. mIL-18 was preincubated with the proteins for 20 min at room temperature prior to addition to cells. The amount of Fc protein was titrated from 1 ug/ml to 50 ug/ml. Cells were stimulated 4 hours, then lysed and luciferase activity was assessed using the Promega Luciferase Assay Reagents.

Preincubation of IL-18 with mIL-1Rrp1-Fc, mIL-1Rrp1-FlagpolyHis, or mAcPL-Fc had no significant effect on induction of NFκB at any of the concentrations tested. In contrast, incubation of IL-18 with a heterogeneous mIL-1Rrp1-Fc+mAcPL-Fc protein mixture (consisting of homodimers of mIL-1Rrp1-Fc, homodimers of mAcPL-Fc, and heterodimeric mIL-1Rrp1-Fc/mAcPL-Fc molecules) resulted in a dose-dependent inhibition of NFκB induction. Uninduced cells displayed 3×10e3 RLU, and cells stimulated with mIL-18 in the absence of any receptor-Fc protein displayed 25×10e3 RLU. Maximal inhibition of NFκB induction was observed with 20 ug/ml and 50 ug/ml of mIL-1Rrp1-Fc+mAcPL-Fc protein mixture, which resulted in 6×10e3 RLU, representing an 87% inhibition of IL-18 activity.

What is claimed is:

1. An isolated protein comprising at least one first polypeptide linked to at least one second polypeptide, wherein said first polypeptide binds to IL-18, and further
wherein said first polypeptide is encoded by a DNA selected from the group consisting of:
a) DNA comprising the coding region of the nucleotide sequence presented in SEQ ID NO:7;
b) DNA that is complementary to DNA capable of hybridizing to the DNA of (a) under highly stringent conditions (hybridization at 68° C. followed by washing in 0.1×SSC/0.1% SDS at 63-68° C.); and,
c) DNA that encodes a polypeptide comprising the amino acid sequence presented in SEQ ID NO:8; and, wherein said second polypeptide is encoded by a DNA selected from the group consisting of:

a') DNA comprising the coding region of the nucleotide sequence presented in SEQ ID NO:5;
b') DNA that is complementary to DNA capable of hybridizing to the DNA of (a') under highly stringent conditions (hybridization at 68° C. followed by washing in 0.1×SSC/0.1% SDS at 63-68° C.); and
c') DNA that encodes a polypeptide comprising the amino acid sequence presented in SEQ ID NO:6, wherein the isolated protein binds IL-18 with an affinity greater than that of the first polypeptide alone.

2. An isolated protein comprising at least one first polypeptide linked to at least one second polypeptide, wherein said first polypeptide binds to IL-18, and further
wherein said first polypeptide is encoded by a DNA selected from the group consisting of:
a) DNA encoding a polypeptide comprising amino acids y-325 of SEQ ID NO:8, wherein y represents an integer between and including 1 and 19; and
b) DNA that is complementary to DNA capable of hybridizing to the DNA of a) under highly stringent conditions (hybridization at 68° C. followed by washing in 0.1× SSC/0.1% SDS at 63-68° C.); and
wherein said second polypeptide is encoded by a DNA selected from the group comprising:
a') DNA encoding a polypeptide comprising amino acids x-356 of SEQ ID NO:6, wherein x is an integer between and including 1 and 15; and
b') DNA that is complementary to DNA capable of hybridizing to the DNA of a') under highly stringent conditions (hybridization at 68° C. followed by washing in 0.1× SSC/0.1% SDS at 63-68° C.),
wherein the isolated protein binds IL-18 with an affinity greater than that of the first polypeptide alone.

3. An isolated protein comprising at least one first polypeptide linked to at least one second polypeptide, wherein the second polypeptide comprises a polypeptide having amino acids x-356 of SEQ ID NO:6, wherein x is an integer between and including 1 and 15; and wherein the first polypeptide binds to IL-18, and further wherein said first polypeptide comprises a polypeptide having amino acids y-325 of SEQ ID NO:8, wherein y represents an integer between and including 1 and 19; and, further wherein the isolated protein binds IL-18 with an affinity greater than that of the first polypeptide alone.

4. A protein having a formula selected from the group consisting of:

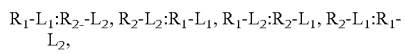

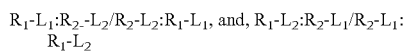

wherein $L_1$ is an immunoglobulin heavy chain fragment; $L_2$ is an immunoglobulin light chain fragment; : is a linkage between a heavy chain and light chain antibody region, / is a linkage between a light chain and a heavy chain antibody region; and
wherein $R_2$ is selected from the group consisting of:
a) a polypeptide comprising amino acids y-325 of SEQ ID NO:8, wherein y represents an integer between and including 1 and 19; and
b) a fragment of the polypeptide of a), and further
wherein $R_2$ binds IL-18;
wherein said $R_1$ is selected from the group consisting of:
a') a polypeptide comprising amino acids x-356 of SEQ ID NO:6, wherein x represents an integer between and including 1 and 15;
b') a fragment of the polypeptide of a'), and further
wherein the protein binds IL-18 with an affinity greater than that of $R_2$ alone.

5. An isolated protein comprising at least one first polypeptide linked to at least one second polypeptide, wherein the first polypeptide comprises amino acids 19 through 325 of SEQ ID NO:8 and the second polypeptide comprises amino acids 15 through 356 of SEQ ID NO:6.

6. The isolated protein of claim 5, wherein the first polypeptide and second polypeptide are linked via a peptide linker.

7. A heterodimeric protein comprising a first fusion polypeptide and a second fusion polypeptide, the first fusion polypeptide comprising an antibody light chain polypeptide attached to the C-terminus of a soluble first polypeptide or a soluble second polypeptide, and the second fusion polypeptide comprising an antibody heavy chain polypeptide attached to the C-terminus of a soluble first polypeptide or of a soluble second polypeptide, wherein said first fusion polypeptide is linked to said second fusion polypeptide via disulfide bonds between the heavy chain and light chain polypeptides; and,
wherein the soluble first polypeptide is selected from the group consisting of:
a) polypeptides comprising amino acids y-325 of SEQ ID NO:8, wherein y represents an integer between and including 1 and 19; and,
b) polypeptides comprising a fragment of a),
further wherein the first soluble polypeptide binds IL-18; and
wherein the soluble second polypeptide is selected from the group consisting of:
a') polypeptides comprising amino acids x-356 of SEQ ID NO:6, wherein x represents an integer between and including 1 and 15; and
b') polypeptides comprising a fragment of a'), wherein the fragment of a'), in combination with soluble first polypeptide binds IL-18 with an affinity greater than that of the soluble first polypeptide alone.

8. A protein having a formula selected from the group consisting of:

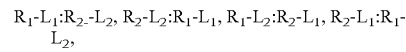

wherein $L_1$ comprises an immunoglobulin heavy chain fragment; $L_2$ comprises an immunoglobulin light chain fragment; $R_1$ comprises a fragment of SEQ ID NO:6; $R_2$ comprises a fragment of SEQ ID NO:8: is a linkage between a heavy chain and light chain antibody region, and / is a linkage between a light chain and heavy chain antibody region,
wherein the fragment of SEQ ID NO:8 binds IL-18, and further
wherein the protein binds IL-18 with higher affinity than the fragment of SEQ ID NO:8 alone.

9. A protein comprising at least one first polypeptide linked to at least one second polypeptide wherein the first polypeptide comprises a fragment of amino acids 1-325 of SEQ ID NO:8 that binds IL-18 and the second polypeptide comprises a fragment of amino acids 1-356 of SEQ ID NO:6, wherein the protein binds IL-18 with a greater affinity than amino acids 1-325 of SEQ ID NO:8 alone.

10. A host cell genetically engineered to express a protein selected from the group consisting of the protein of claim 1, the protein of claim 2, the protein of claim 3, and the protein of claim 4.

11. A process of comprising culturing the host cell of claim 10 under conditions that promote expression of the protein.

12. A composition comprising a protein selected from the group consisting of the protein of claim 1, the protein of claim 2, the protein of claim 3, and the protein of claim 4.

13. A method of inhibiting the effects of IL-18 comprising administering an effective amount of the composition of claim 12 to a mammal in need thereof.

* * * * *